US00RE41151E

(19) United States
(12) Reissued Patent
Lai et al.

(10) Patent Number: US RE41,151 E
(45) Date of Reissued Patent: Feb. 23, 2010

(54) PROTECTED FORMS OF PHARMACOLOGICALLY ACTIVE AGENTS AND USES THEREOF

(75) Inventors: Ching-San Lai, Encinitas, CA (US); Tingmin Wang, San Marcos, CA (US)

(73) Assignee: Medinox, Inc., Carlsbad, CA (US)

(21) Appl. No.: 12/194,940

(22) Filed: Aug. 20, 2008

Related U.S. Patent Documents

Reissue of:
(64) Patent No.: 6,355,666
Issued: Mar. 12, 2002
Appl. No.: 09/602,688
Filed: Jun. 23, 2000

(51) Int. Cl.

| | |
|---|---|
| ***A61K 31/48*** | (2006.01) |
| ***A61K 31/405*** | (2006.01) |
| ***A61K 31/255*** | (2006.01) |
| ***A61K 31/40*** | (2006.01) |
| ***A61K 31/34*** | (2006.01) |
| ***C07C 69/66*** | (2006.01) |
| ***C07C 69/67*** | (2006.01) |
| ***C07C 69/612*** | (2006.01) |

(52) U.S. Cl. ..... 560/56; 514/411; 514/415; 514/424; 514/517; 514/532; 514/533; 514/534; 548/366.7; 548/367.1; 548/449; 548/486; 558/52; 558/56; 560/60; 560/73; 564/92; 564/167; 564/168; 564/160; 564/163

(58) Field of Classification Search ..... 560/56
See application file for complete search history.

(56) References Cited

U.S. PATENT DOCUMENTS

| | | | |
|---|---|---|---|
| 4,362,738 | A | 12/1982 | Keck et al. |
| 5,077,217 | A | 12/1991 | Matson et al. |
| 5,214,191 | A | 5/1993 | Kirschenheuter et al. |
| 5,663,416 | A | 9/1997 | Kirschenheuter et al. |
| 5,703,073 | A | 12/1997 | Garvey et al. |
| 5,916,910 | A | 6/1999 | Lai |
| 5,925,673 | A | 7/1999 | Hellberg et al. |
| 6,177,466 | B1 | 1/2001 | Sakaki et al. |
| 6,201,151 | B1 | 3/2001 | Tsai et al. |
| 6,297,260 | B1 | 10/2001 | Bandarage et al. |
| 6,306,842 | B1 | 10/2001 | Lai et al. |
| 2006/0046967 | A1 | 3/2006 | Satyam |

FOREIGN PATENT DOCUMENTS

| | | | |
|---|---|---|---|
| CA | 1140564 | | 2/1983 |
| DE | 2926472 | | 1/1981 |
| EP | 24282 | | 3/1981 |
| EP | 0461043 | A2 | 12/1991 |
| EP | 0034871 | B2 | 8/1993 |
| EP | 0035305 | B2 | 9/1996 |
| GB | 1125410 | A | 8/1968 |
| JP | 64040458 | | 2/1989 |
| JP | 64-040458 | | 10/1989 |
| JP | 05-279330 | | 10/1993 |
| WO | 98/16502 | A1 | 4/1998 |
| WO | 2001/062085 | A1 | 8/2001 |
| WO | 03/045896 | A1 | 6/2003 |
| WO | 2004/004648 | A2 | 1/2004 |

OTHER PUBLICATIONS

Datta et al., Catalytically Distinct Antibodies Prepared by the Reactive Immunization versus Transition State Analogue Hapten Manifolds, 1999, J. Am. Chem. Soc. 121(45):10461–10467.

Lo et al., Reactive Immunization Strategy Generates Antibodies with High Catalytic Proficiencies, 1997, J. Am. Chem. Soc. 119(42):10251–10252.

Alonso et al., η–Deficient 2–(Arylsulfonyl) Ethyl Esters as Protecting Groups for Carboxylic Acids, 2003, Synthesis 2:277–287, Verlag.

Sarakinos et al., A Practical New Chiral Controller for Asymmetric Diels–Alder and Alkylation Reactions, 1999, Organic Letters 1(11):1741–1744.

Schnitzer et al., Double–Blind, Placebo–Controlled Comparison of the Safety and Efficacy of Orally Administered Etodolac and Nabumetone in Patients with Active Osteoarthritis of the Knee, 1995, Clinical Thera. 17(4):602–612.

Weaver et al., Comparison of the Efficacy and Safety of Oxaprozin and Nabumetone in the Treatment of Patients with Osteoarthritis of the Knee, 1995, Clinical Thera. 17(4):735–745.

Fleischmann et al., A Double–Masked Comparison of Naprelan and Nabumetone in Osteoarthritis of the Knee, 1997, Clinical Thera. 19(4):642–655.

Lipscomb et al., Gastric mucosal injury and adaption to oral and rectal administration of naproxen, 1996, Aliment Pharmacol. Ther. 10:133–138.

Hawthorne et al., Aspirin–induced gastric mucosal damage: prevention by enteric–coating and relation to prostaglandin synthesis, 1991, Br. J. Clin. Pharmac. 32:77–83.

Kelly et al., Risk of aspirin–associated major upper–gastrointestinal bleeding with enteric–coated or buffered product, 1996, The Lancet 348:1413–1416.

Evans et al., Topical non–steroidal anti–inflammatory drugs and admission to hospital for upper gastrointestinal bleeding and performation: a record linkage case–control study, 1995, BMJ 311:22–26.

Weil et al., Prophylactic aspirin and risk of peptic ulcer bleeding, 1995, BMJ 310:827–830.

(Continued)

*Primary Examiner*—Laura L. Stockton
(74) *Attorney, Agent, or Firm*—Pepper Hamilton LLP

(57) ABSTRACT

In accordance with the present invention, there are provided normal modified forms of nonsteroidal anti-inflammatory drugs. Modified NSAIDs according to the invention provide a new class of anti-inflammatory agent which provide the therapeutic benefits of NSAIDs while causing a much lower incidence of side-effects then typically observed with such agents.

8 Claims, 3 Drawing Sheets

OTHER PUBLICATIONS

Banoob et al., Risk of gastric injury with enteric–versus non-enteric–coated aspirin, 2002, Ann. Pharmacother. 36:163–166.
Lanza et al., Endoscopic evaluation of the effects of aspirin, buffered aspirin, and enteric–coated aspirin on gastric and duodenal mucosa, 1980, N. Eng. J. Med. 303:136–138.
Petroski, Endoscopic comparison of three aspirin preparations and placebo, 1993, Clin. Ther. 15:314–320.
Lanza et al., Reduction in gastric mucosal hemorrhage and ulceration with chronic high–level dosing of enteric–coated aspirin granules two and four times a day, 1985, Dig. Dis. Sci. 30:509–512.
Hoftiezer et al., Comparison of the effects of regular and enteric–coated aspirin on gastroduodenal mucosa of man, 1980, The Lancet 2:609–612.
Lengeling et al., Ulcerative ileitis encountered at ileo–colonoscopy: likely role of nonsteroidal agents, 2003, Clin. Gastroenterol. Hepatol. 1:160–169.
Puspok et al., Clinical, endoscopic, and histologic spectrum of nonsteroidal anti–inflammatory drug–induced lesions in the colon, 2000, Dis. Colon Rectum 43:685–691.
Kato et al., Cycloxygenase–1 and Cyclooxygenase–2 selectivity of non–steroidal anti–inflammatory drugs: investigation using human peripheral monocytes, 2001, J. Pharm. Pharmacol. 53:1679–1685.
Bianchi Porro et al., Gastroduodenal tolerability of Nabumetone versus naproxen in the treatment of rheumatic patients, 1995, Am. J. Gastroenterol. 90:1485–1488.
Roth et al., A controlled study comparing the effects of Nabumetone, ibuprofen, and ibuprofen plus misoprostol on the upper gastrointestinal tract mucosa, 1993, Arch. Intern. Med. 153:2565–2571.
Greb et al. Endoscopic studies of Nabumetone in patients with rheumatoid arthritis: a comparative endoscopic and histologic evaluation, 1987, Am. J. Med. 83(4B):19–24.
Roth, Sanford H., Endoscopy–controlled study of the safety of Nabumetone compared with naproxen in arthritis therapy, 1987, Am. J. med. 30(4B):25–30.
Weaver et al., Treatment of patients with osteoarthritis with rofecoxib compared with Nabumetone, 2006, J. Clin. Rheumatol. 12:17–25.
Kivitz et al., Efficacy and safety of refecoxib 12.5 mg versus Nabumetone 1,000 mg in patients with osteoarthritis of the knee: a randomized controlled trial, 2004, J. Am. Geriatric Soc. 52:666–674.
Van Gossum et al., Anorectal stenosis in patients with prolonged use of suppositories containing paracetamol and acetylsalicylic acid, 1993, Dig. Dis. Sci. 38:1970–1977.
D'Haens et al., Procitis and Rectal Stenosis Induced by Nonsteroidal Anti–inflammatory Suppositories, 1993, J. Clin. Gastroenterol. 17(3):207–212.
Ivey et al., Acute effect of systemic aspirin on gastric mucosa in man, 1980, Dig. Dis. Sci. 25:97–99.
Baskin et al., Aspirin–induced ultrastructural changes in human gastric mucosa: correlation with potential difference, 1976, Ann. Intern. Med. 85:299–303.
Evans et al., Non–steroidal anti–inflammatory drugs and hospitalization for acute renal failure, 1995, QJM 88:551–557.
Goldstein et al., Reduced incidence of gastroduodenal ulcers with celecoxib, a novel cyclooxygenase–2 inhibitor, compared to naproxen in patients with arthritis, 2001, Am. J. Gastroenterol. 96:1019–1027.
Wolfe et al., Giant duodenal ulcers associated with the post-operative use of ketorolac: report of three cases, 1994, Am. J. Gastroenterol. 89:1110–1111.
Traversa et al., Gastroduodenal toxicity of different nonsteroidal anti–inflammatory drugs, 1995, Epidemiology 6:49–54.
Lanas et al., Risk of upper gastrointestinal ulcer bleeding associated with selective cyclo–oxygenase–2 inhibitors, traditional non–aspirin NSAIDs, aspirin, and combinations, 2006, Gut 55:1731–1738.
Hansen et al., Comparison of intravenous and intragastric aspirin in production of antral gastric ulcers in cats, 1980, Proc. Soc. Exp. Biol. Med. 164:589–592.
Ligumsky et al., Rectal Administration of Nonsteroidal Anti-inflammatory Drugs: effect on rat gastric ulcerogenicity and prostaglandin $E_2$synthesis, 1990, Gastroenterology 98:1245–1249.
Ogiso et al., Pharmacokinetics of Indomethacin Ester Prodrugs: Gastrointestinal and Hepatic Toxicity and the Hydrolytic Capacity of Various Tissues in Rats, 1996, Biol. Pharm. Bull. 19(9):1178–1183.
Giraud et al., Interaction of Indomethacin and Naproxen with Gastric Surface–active Phospholipids: A Possible Mechanism for the Gastric Toxicity of Nonsteroidal Anti–Inflammatory Drugs (NSAIDS), 1999, Biochem. Pharmacol. 57:247–254.
Marzo et al., Absorption and Distribution of Naproxen in Rats Orally Treated with Naproxen Betainate Sodium Salt Monohydrate, 1997, Arzneim. Forsch/Drug Res. 47(1):381–384.
Bjarnason et al., Side Effects of Nonsteroidal Anti–inflammatory Drugs on the Small and Large Intestine in Humans, Special Reports and Reviews, 1993, Gastreoenterology 104:1832–1847.
Carson et al., The Relative Gastrointestinal Toxicity of the Nonsteroidal Anti–inflammatory Drugs, 1987, Arch. Intern. Med. vol. 147, Jun. pp. 1054–1059.
Glaser et al., Etodolac Selectively Inhibits Human Prostaglandin G/H Synthase 2 (PGHS–2) Versus Human PGHS–1, 1995, European J. Pharmacol. 281:107–111.
Graham et al., Nonsteroidal Anti–Inflammatory Effect of Sulindac Sulfoxide and Sulfide on Gastric Mucosa, 1985, Clin. Pharmacol. Ther. 38:65–70.
Kaplan–Machlis et al., The Cyclooxygenase–2 Inhibitors: Safety and Effectiveness, 1999, The Annals of Pharmacotherapy, 33:979–988, Sep.
Kargman et al., Characterization of Prostaglandin G/H Synthase 1 and 2 in Rat, Dog, Monkey and Human Gastrointestinal Tracts, 1996, Gastroenterology, American Gastroenterological Association 111:445–454.
Meade et al., Differential Inhibition of Prostaglandin Endoperoxide Synthase (Cyclooxygenase) Isozymes by Aspirin and Other Non–steroidal Anti–inflammatory Drugs, 1993, J. Biol. Chem., The American Soc. for Biochem. and Molecular Biology, Inc., vol. 268(9):6610–6614, Mar. 25.
Mitchell et al., Selectivity of Nonsteroidal Antiinflammatory Drugs as Inhibitors of Constitutive and Inducible Cyclooxygenase, 1994, Proc. Natl. Acad. Sci. USA, Pharmacology 90:11693–11697, Dec.
Onoe et al., IL–13 and IL–4 Inhibit Bone Resorption by Suppressing Cyclooxygenase–2–Dependent Prostaglandin Synthesis in Osteoblasts, 1996, J. Immunol. The American Assoc. of Immunol. 156:758–764.

Slater et al., Expression of Cyclooxygenase Types 1 and 2 in Human Fetal Membranes at Term, 1995, Am. J. Obstet. Gynecol. 172(1, Part 1):77–82.
Soll et al., Nonsteroidal Antiinflammatory Drugs and Peptic Ulcer Disease, 1991, Annals of internal Medicine (UCLA Conference) 114:307–319.
Wallace et al., Nonsteroidal Anti–inflammatory Drugs and Gastroenteropathy: The Second Hundred Years, 1997, Gastroenterology, The American Gastroenterological Association 112:1000–1016.
Datta et al., Catalytically Distinct Antibodies Prepared by the Reactive Immunization versus Transition State Analogue Hapten Manifolds, 1999, J. Am. Chem. Soc. 121:10461–10467.
Lo et al., Reactive immunization Strategy Generates Antibodies with High Catalytic Proficiencies, 1997, J. Am. Chem. Soc. 119:10251–10252.
Kirschenheuter et al., Synthesis and Characterization of Human Neutrophil Elastrase Inhibitors Derived from Aromatic Esters of Phenylalkanoic Acids, in Proteases, Protease Inhibitors and Protease–Derived Peptides, Birkhauser Verlag, Basel, 1993, pp. 71–82.
Alonso et al., π–Deficient 2–(Arysulfonyl)ethyl Esters as Protecting Groups for Carboxylic Acids, 2002, Synthesis 2:277–287.
Zheng et al., Synthesis of antiinflammatory analgesic bisphophonate compounds, Hecheng Huaxue, 7(4):427–429, 1999—English Abstract only.

PROTECTED FORMS OF PHARMACOLOGICALLY ACTIVE AGENTS AND USES THEREOF

Matter enclosed in heavy brackets [ ] appears in the original patent but forms no part of this reissue specification; matter printed in italics indicates the additions made by reissue.

*This application is a reissue for U.S. Pat. No. 6,355,666 entitled "Protected Forms of Pharmacologically Active Agents and Uses Therefor," which matured from U.S. application Ser. No. 09/602,688 filed on Jun. 23, 2000, which is hereby incorporated by reference in its entirety.*

FIELD OF THE INVENTION

The present invention relates to novel forms of pharmacologically active agents, and methods for the preparation and use thereof. In a particular aspect of the invention, methods are provided for treating pathological conditions with a protected form of one or more pharmacologically active agents, thereby reducing the occurrence of side-effects caused thereby.

BACKGROUND OF THE INVENTION

Despite the advent of modem pharmaceutical technology, many drugs still possess untoward toxicities which often limit the therapeutic potential thereof. For example, although non-steroid anti-inflammatory drugs (NSAIDs) are a class of compounds which are widely used for the treatment of inflammation, pain and fever, NSAIDs (e.g., naproxen, aspirin, ibuprofen and ketoprofen) can cause gastrointestinal ulcers, a side-effect that remains the major limitation to the use of NSAIDs (see, for example, J. L. Wallace, in Gastroenterol. 112:1000–1016 (1997); A. H. Soll et al., in Ann Intern Med. 114:307–319 (1991); and J. Bjarnason et al., in Gastroenterol. 104:1832–1847 (1993)).

There are two major ulcerogenic effects of NSAIDs: (1) irritant effects on the epithelium of the gastrointestinal tract and (2) suppression of gastrointestinal prostaglandin synthesis. In recent years, numerous strategies have been attempted to design and develop new NSAIDs that reduce the damage to the gastrointestinal tract. These efforts, however, have largely been unsuccessful. For example, enteric coating or slow-release formulations designed to reduce the topical irritant properties of NSAIDs have been shown to be ineffective in terms of reducing the incidence of clinically significant side effects, including perforation and bleeding (see, for example, D. Y. Graham et al., in Clin. Pharmacol. Ther. 38:65–70 (1985); and J. L. Carson, et al., in Arch. Intern. Med., 147:1054–1059 (1987)).

It is well recognized that aspirin and other NSAIDs exert their pharmacological effects through the non-selective inhibition of cyclooxygenase (COX) enzymes, thereby blocking prostaglandin synthesis (see, for example, J. R. Van in Nature, 231:232–235 (1971)). There are two types of COX enzymes, namely COX-1 and COX-2. COX-1 is expressed constitutively in many tissues, including the stomach, kidney, and platelets, whereas COX-2 is expressed only at the site of inflammation (see, for example, S. Kragan et al. in Gastroenterol., 111:445–454 (1996)). The prostagladins derived from COX-1 are responsible for many of the physiological effects, including maintenance of gastric mucosal integrity.

Many attempts have been made to develop NSAIDs that only inhibit COX-2, without impacting the activity of COX-1 (see, for example, J. A. Mitchell et al., in Proc. Natl. Acad. Sci. USA 90:11693–11697 (1993); and E. A. Meade et al., in J. Biol. Chem., 268:6610–6614 (1993)). There are several NSAIDs presently on the market (e.g., rofecoxib and celecoxib) that show marked selectivity for COX-2 (see, for example, E. A. Meade, supra.; K. Glaser et al., in Eur. J. Pharmacol. 281:107–111 ((1995) and Kaplan-Machlis, B., and Klostermeyer, BS in Ann Pharmacother. 33:979–88, (1999)). These drugs appear to have reduced gastrointestinal toxicity relative to other NSAIDs on the market.

On the basis of encouraging clinical as well as experimental data, the development of highly selective COX-2 inhibitors appears to be a sound strategy to develop a new generation of anti-inflammatory drugs. However, the physiological functions of COX-1 and COX-2 are not always well defined. Thus, there is a possibility that prostagladins produced as a result of COX-1 expression may also contribute to inflammation, pain and fever. On the other hand, prostagladins produced by COX-2 have been shown to play important physiological functions, including the initiation and maintenance of labor and in the regulation of bone resorption (see, for example, D. M. Slater et al., in Am. J. Obstet. Gynecol., 172:77–82 (1995); and Y. Onoe et al., in J. Immunol. 156:758–764 (1996)), thus inhibition of this pathway may not always be beneficial. Considering these points, highly selective COX-2 inhibitors may produce additional side effects above and beyond those observed with standard NSAIDs, therefore such inhibitors may not be highly desirable.

Accordingly, there is still a need in the art for modified forms of NSAIDs which cause a reduced incidence of side-effects, relative to the incidence of side-effects caused by such pharmacologically active agents in unmodified form.

BRIEF DESCRIPTION OF THE INVENTION

In accordance with the present invention, there is provided a new class of modified NSAIDs which cause a much lower incidence of side-effects than are typically observed with unmodified NSAIDs due to the protective effects imparted by modifying the NSAIDs as described herein.

There are a number of advantages provided by modified NSAIDs according to the invention including:

(i) reduced irritant effects (e.g., contact irritation) of NSAIDs, and (ii) enhanced tissue delivery of the drug as a result of a decrease in net charges on the molecule, particularly for acidic NSAIDs such as naproxen, aspirin, diclofenac and ibuprofen, thereby reducing the quantity of material which must be delivered to achieve an effective dosage.

In accordance with the present invention, cleavage of the modified NSAIDs described herein from the modified group appended thereto releases the pharmaceutically active agent.

DETAILED DESCRIPTION OF THE INVENTION

Figure 1:
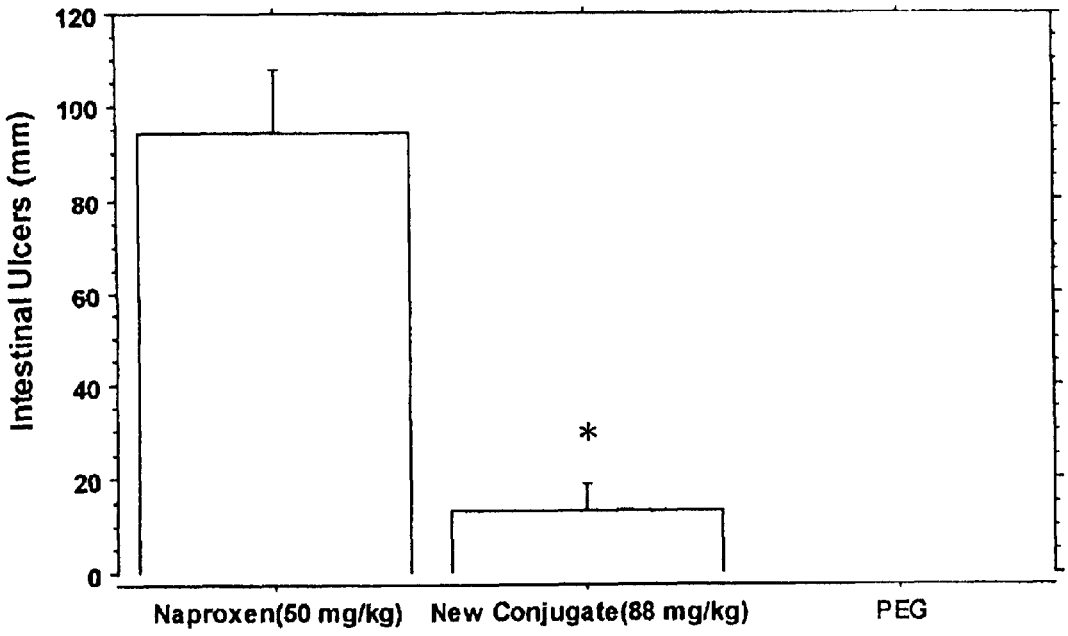
FIG. 1 illustrates the total length of intestinal ulcers measured after three daily doses of NSAID in unfasted male Sprague-Dawley rats (150–200 g) treated with vehicle, naproxen or equimolar invention composition (compound 19). * $P<0.05$ by unpaired t-test.

In accordance with the present invention, there are provided compounds comprising a modified NSAID, wherein the NSAID is covalently attached either directly or through a linker molecule to a sulfur-containing functional group containing an optionally substituted hydrocarbyl moiety. Invention compounds have the structure:

X—L—Z wherein:

X=a non-steroidal anti-inflammatory drug (NSAID),

L=an optional linker/spacer, and

Z=a sulfur-containing functional group containing an optionally substituted hydrocarbyl moiety.

NSAIDs contemplated for modification in accordance with the present invention include acetaminophen (Tylenol, Datril, etc.), aspirin, ibuprofen, Motrin, Advil, Rufen, others), choline magnesium salicylate (Triasate), choline salicylate (Anthropan), diclofenac (voltaren, cataflam), diflunisal (dolobid), etodolac (lodine), feoprofen calcium (nalfon), flurbiprofen (ansaid), indomethacin (indocin, indometh, others), ketoprofen (orudis, oruvail), carprofen, indoprofen, ketorolac tromethamine (toradol), magnesium salicylate (Doan's, magan, mobidin, others), meclofenamate sodium (meclomen), mefenamic acid (relafan), oxaprozin (daypro), piroxicam (feldene), sodium salicylate, sulindac (clinoril), tolmetin (tolectin), meloxicam, nabumetone, naproxen, lornoxicam, nimesulide, indoprofen, remifenzone, salsalate, tiaprofenic acid, flosulide, and the like. Presently preferred NSAIDs employed in the practice of the invention include naproxen, aspirin, ibuprofen, flurbiprofen, indomethacin, ketoprofen, carprofen, and the like.

Invention compounds can be readily prepared in a variety of ways either by direct reaction of NSAIDs with the sulfur-containing functional group or indirectly through a suitable linker molecule.

The components of invention compositions are directly or indirectly covalently attached employing a variety of linkages (including an optional linker), e.g., ester linkages, disulfide linkages, amide linkages, imine linkages, enamine linkages, ether linkages, thioether linkages, imide linkages, sulfate ester linkages, sulfonate ester linkages, sulfone linkages, sulfonamide linkages, phosphate ester linkages, carbonate linkages, O-glycosidic linkages, S-glycosidic linkages, and the like. Such linkages can be accomplished using standard synthetic techniques as are well known by those of skill in the art, either by direct reaction of the starting materials, or by incorporating a suitable functional group on the starting material, followed by coupling of the reactants.

When the pharmacologically active agents contemplated for use herein contain suitable functionality thereon, e.g., hydroxy, amino, carboxy, and the like, invention modified NSAIDs can be prepared by direct linkage between the two agents. Alternatively, the NSAIDs can be functionalized so as to facilitate linkage between the two agents. When present, linker/spacer L has the following structure:

—W—R— wherein:

R is optional, and when present is alkylene, substituted alkylene, cycloakylene, substituted cycloaklylene, heterocyclic, substituted heterocyclic, oxyalkylene, substituted oxyalkylene, alkylene, substituted alkyenylene, arylene, substituted arylene, alkarylene, substituted alkarylene, aralkylene or substituted aralkylene, and W is ester, reverse ester, thioester, reverse thioester, amide, reverse amide, phosphate, phosphonate, imine, enamine, or the like.

Functional groups contemplated by the present invention are sulfur-based. Examples of suitable sulfur-containing functional groups include sulfonate, reverse sulfonate, sulfonamide, reverse sulfonamide, sulfone, sulfinate, reverse sulfinate, and the like. In a particular aspect of the invention, the sulfur-based moiety is sulfonate or reverse sulfonate. In a particularly preferred aspect of the invention, the sulfonate is an optionally substituted aromatic sulfoante such as tosylate or brosylate.

Other preferred sulfur-based functional groups contemplated by the present invention include sulfones. Preferably, the sulfone is an optionally substituted alkyl or aromatic sulfone.

In one aspect of the invention, Z may have the following structure:

$$—Y—S(O)_n—Y'—Q$$

wherein:

each of Y and Y' are optionally present, and when present are independently —O— or —NR'—, wherein R' is H or an optionally substituted hydrocarbyl moiety;

n is 1 or 2, and

Q is H or an optionally substituted hydrocarbyl moiety.

As employed herein, "hydrocarbyl" embraces alkyl, substituted alkyl, oxyalkyl, substituted oxyalkyl, cycloalkyl, substituted cycloalkyl, alkenyl, substituted alkenyl, alkynyl, substituted alkynyl, monocyclic heterocyclic, substituted monocylic heterocyclic, monocyclic aromatic, monosubstituted monocyclic aromatic, or the like.

As employed herein, "alkyl" refers to hydrocarbyl radicals having 1 up to 20 carbon atoms, preferably 2–10 carbon atoms; and "substituted alkyl" comprises alkyl groups further being one or more substituents selected from hydroxy, alkoxy (of a lower alkoxy group), mercapto (of a lower alkyl group), cycloalkyl, substituted cycloalkyl, heterocyclic, substituted heterocyclic, aryl, substituted aryl, heteroaryl, substituted heteroaryl, aryloxy, substituted aryloxy, halogen, trifluoromethyl, cyano, nitro, nitrone, amino, amido, —C(O)H, acyl, oxyacyl, carboxyl, carbamate, sulfonyl, sulfonamide, sulfuryl, and the like.

As employed herein, "oxyalkyl" refers to the moiety —O-alkyl-, wherein alkyl is as defined above, and "substituted oxyalkyl" refers to oxyalkyl groups further bearing one or more substituents as set forth above.

As employed herein, "cycloalkyl" refers to cyclic ring-containing groups containing in the range of about 3 up to 8 carbon atoms, and "substituted cycloalkyl" refers to cycloalkyl groups further bearing one or more substituents as set forth above.

As employed herein, "heterocyclic" refers to cyclic (i.e., ring-containing) groups containing one or more heteroatoms (e.g., N, O, S, or the like) as part of the ring structure, and having in the range of 3 up to 14 carbon atoms and "substituted heterocyclic" refers to heterocyclic groups further bearing one or more substituents as set forth above.

As employed herein, "alkenyl" refers to straight or branched chain hydrocarbyl groups having at least one carbon-carbon double bond, and having in the range of about 2 up to 12 carbon atoms, and "substituted alkenyl" refers to alkenyl groups further bearing one or more substituents as set forth above.

As employed herein, "alkynyl" refers to straight or branched chain hydrocarbyl groups having at least one carbon-carbon triple bond, and having in the range of about 2 up to 12 carbon atoms, and "substituted alkynyl" refers to alkynylene groups further bearing one or more substituents as set forth above.

As employed herein, "monocyclic aromatic" refers to aromatic groups having in the range of 5 up to 7 carbon atoms and "monosubstituted monocyclic aromatic" refers to aromatic groups further bearing one of the substituents set forth above.

As employed herein, "alkylene" refers to divalent hydrocarbyl radicals having 1 up to 20 carbon atoms, preferably 2–10 carbon atoms; and "substituted alkylene" comprises alkylene groups further bearing one or more substituents as set forth above.

As employed herein, "cycloalkylene" refers to cyclic ring-containing groups containing in the range of about 3 up to 8 carbon atoms, and "substituted cycloalkylene" refers to cyclocalkylene groups further bearing one or more substituents as set forth above.

As employed herein, "oxyalkylene" refers to the moiety —O-alkylene-, wherein alkylene is as defined above, and "substituted oxyalkylene" refers to oxyalkylene groups further bearing one or more substituents as set forth above.

As employed herein, "alkylene" refers to divalent, straight or branched chain hydrocarbyl groups having at least one carbon-carbon double bond, and having in the range of about 2 up to 12 carbon atoms, and "substituted alkylene" refers to alkylene groups further bearing one or more substituents as set forth above.

As employed herein, "alkynylene" refers to divalent straight or branched chain hydrocarbyl groups having at least one carbon-carbon triple bond, and having in the range of about 2 up to 12 carbon atoms, and "substituted alkynylene" refers to alkynylene groups further bearing one or more substituents as set forth above.

As employed herein, "arylene" refers to divalent aromatic groups having in the range of 6 up to 14 carbon atoms and "substituted arylene" refers to arylene groups further bearing one or more substituents as set forth above.

As employed herein, "alkylarylene" refers to alkyl-substituted arylene groups and "substituted alkylarylene" refers to alkylarylene groups further bearing one or more substituents as set forth above.

As employed herein, "arylalkylene" refers to aryl-substituted alkylene groups and "substituted arylalkylene" refers to arylalkylene groups further bearing one or more substituents as set forth above.

As employed herein, "arylalkenylene" refers to aryl-substituted alkylene groups and "substituted arylalkenylene" refers to arylalkenylene groups further bearing one or more substituents as set forth above.

As employed herein, "arylalkynylene" refers to aryl-substituted alkynylene groups and "substituted arylalkynylene" refers to arylalkynylene groups further bearing one or more substituents as set forth above.

Diseases and conditions contemplated for treatment in accordance with the present invention include inflammatory and infectious diseases, such as, for example, septic shock, hemorrhagic shock, anaphylactic shock, toxic shock syndrome ischemia, cerebral ischemia, administration of cytokines, overexpression of cytokines, ulcers, inflammatory bowel disease (e.g., ulcerative colitis or Crohn's disease), diabetes, arthritis, asthma, Alzheimer's disease, Parkinson's disease, multiple sclerosis, cirrhosis, allograft rejection, encephalomyelitis, meningitis, pancreatitis, peritonitis, vasculitis, lymphocytic choriomeningitis, glomerulonephritis, uveitis, ileitis, inflammation (e.g., liver inflammation, renal inflammation, and the like), burn, infection (including bacterial, viral, fungal and parasitic infections), hemodialysis, chronic fatigue syndrome, stroke, cancers (e.g., breast, melanoma, carcinoma, and the like), cardiopulmonary bypass, ischemic/reperfusion injury, gastritis, adult respiratory distress syndrome, cachexia, myocarditis, autoimmune disorders, eczema, psoriasis, heart failure, heart disease, atherosclerosis, dermatitis, uticaria, systemic lupus erythematosus, AIDS, AIDS dementia, chronic neurodegenerative disease, chronic pair, priapism, cystic fibrosis, amyotrophic lateral sclerosis, schizophrenia, depression, premenstrual syndrome, anxiety, addiction, migraine, Huntington's disease, epilepsy, neurodegenerative disorders, gastrointestinal motility disorders, obesity, hyperphagia, solid tumors (e.g., neuroblastoma), malaria, hematologic cancers, myelofibrosis, lung injury, graft-versus-host disease, head injury, CNS trauma, hepatitis, renal failure, liver disease (e.g., chronic hepatitis C), drug-induced lung injury (e.g., paraquat), myasthenia gravis (MG), opthalmic diseases, post-angioplasty, restenosis, angina, coronary artery disease, and the like.

In accordance with another embodiment of the present invention, there are provided methods for the preparation of modified NSAIDs, said method comprising covalently attaching a NSAID to a sulfur-containing functional group containing an optionally substituted hydrocabyl moiety. The resulting compound provides a latent form of the pharmacologically active agent, releasing the biological activity thereof only when the compound is cleaved (e.g., by an esterase, amidase or other suitable enzyme).

As readily recognized by those of skill in the art, invention compounds can be prepared in a variety of ways. See, for example, Scheme 1, wherein NSAID, X, bearing a carboxylic moiety can be reacted either directly with the sulfur-containing functional group (Scheme 1a) or indirectly through a linker molecule (Scheme 1b).

Scheme 1a

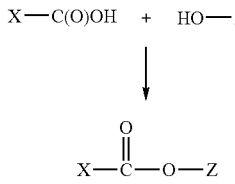

Scheme 1b

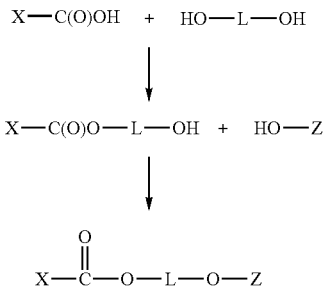

Employing these general reaction schemes, invention modified NSAIDs can be prepared from a wide variety of pharmacologically active agents. See, for example, Examples 1–29 provided herein.

In accordance with yet another embodiment of the present invention, there are provided methods for reducing the side effects induced by administration of NSAIDs to a subject, said method comprising covalently attaching a sulfur-containing functional group containing an optionally substituted hydrocarbyl moiety to said NSAID prior to administration to said subject.

In accordance with still another embodiment of the present invention, there are provided methods for enhancing the effectiveness of NSAIDs, said method comprising covalently attaching a sulfur-containing functional group containing an optionally substituted hydrocarbyl moiety to said NSAID.

In accordance with a still further embodiment of the present invention, there are provided improved methods for the administration of NSAIDs to a subject for the treatment of a pathological condition, the improvement comprising covalently attaching said NSAID to a sulfur-containing functional group containing an optionally substituted hydrocarbyl moiety prior to administration thereof to said subject.

Those of skill in the art recognize that the modified NSAIDs described herein can be delivered in a variety of ways, such as, for example, orally, intravenously, subcutaneously, parenterally, rectally, by inhalation, and the like.

Depending on the mode of delivery employed, the modified NSAIDs contemplated for use herein can be delivered in a variety of pharmaceutically acceptable forms. For example, the invention modified NSAIDs can be delivered in the form of a solid, solution, emulsion, dispersion, micelle, liposome, and the like.

Thus, in accordance with still another embodiment of the present invention, there are provided physiologically active composition(s) comprising invention modified NSAIDs in a suitable vehicle rendering said compounds amenable to oral delivery, transdermal delivery, intravenous delivery, intramuscular delivery, topical delivery, nasal delivery, and the like.

Pharmaceutical compositions of the present invention can be used in the form of a solid, a solution, an emulsion, a dispersion, a micelle, a lipsome, and the like, wherein the resulting composition contains one or more of the modified NSAIDs of the present invention, as an active ingredient, in admixture with an organic or inorganic carrier or excipient suitable for enteral or parenteral applications. Invention modified NSAIDs may be compounded, for example, with the usual non-toxic, pharmaceutically acceptable carriers for tablets, pellets, capsules, suppositories, solutions, emulsions, suspensions, and any other form suitable for use. The carriers which can be used include glucose, lactose, gum acacia, gelatin, mannitol, starch paste, magnesium trisilicate, talc, corn starch, keratin, colloidal silica, potato starch, urea, medium chain length triglycerides, dextrans, and other carriers suitable for use in manufacturing preparations, in solid, semisolid, or liquid form. In addition auxiliary, stabilizing, thickening and coloring agents and perfumes may be used. Invention modified NSAIDs are included in the pharmaceutical composition in an amount sufficient to produce the desired effect upon the process or disease condition.

Pharmaceutical compositions containing invention modified NSAIDs may be in a form suitable for oral use, for example, as tablets, troches, lozenges, aqueous or oily suspension, dispersible powders or granules, emulsions, hard or soft capsules, or syrups or elixirs. Compositions intended for oral use may be prepared according to any method known to the art for the manufacture of pharmaceutical compositions and such compositions may contain one or more agents selected from the group consisting of a sweetening agent such as sucrose, lactose, or saccharin, flavoring agents such as peppermint, oil of wintergreen or cherry, coloring agents and preserving agents in order to provide pharmaceutically elegant and palatable preparations. Tablets containing invention modified NSAIDs in admixture with non-toxic pharmaceutically acceptable excipients may also be manufactured by known methods. The excipients used may be, for example, (1) inert diluents such as calcium carbonate, lactose, calcium phosphate or sodium phosphate; (2) granulating and disintegrating agents such as corn starch, potato starch or aliginic acid; (3) binding agents such as gum tragacanth, corn starch, gelatin or acacia, and (4) lubricating agents such as magnesium stearate, stearic acid or talc. The tablets may be uncoated or they may be coated by known techniques to delay disintegration and absorption in the gastrointestinal tract and thereby provide a sustained action over a longer period. For example, a time delay material such as glyceryl monostearate or glyceryl distearate may be employed. They may also be coated by the techniques described in the U.S. Pat. Nos. 4,256,108; 4,160,452; and 4,265,874, to form osmotic therapeutic tablets for controlled release.

In some cases, formulations for oral use may be in the form of hard gelatin capsules wherein the invention modified NSAIDs are mixed with an inert solid diluent, for example, calcium carbonate, calcium phosphate or kaolin. They may also be in the form of soft gelatin capsules wherein the invention modified NSAIDs are mixed with water or an oil medium, for example, peanut oil, liquid paraffin, or olive oil.

The pharmaceutical compositions may be in the form of a sterile injectable suspension. This suspension may be formulated according to known methods using suitable dispersing or wetting agents and suspending agents. The sterile injectable preparation may also be a sterile injectable solution or suspension in a non-toxic parenterally-acceptable diluent or solvent, for example, as a solution in 1,3-butanediol. Sterile, fixed oils are conventionally employed as a solvent or suspending medium. For this purpose any bland fixed oil may be employed including synthetic mono- or diglycerides, fatty acids (including oleic acid), naturally occurring vegetable oils like sesame oil, coconut oil, peanut oil, cottonseed oil, etc., or synthetic fatty vehicles like ethyl oleate or the like. Buffers, preservatives, antioxidants, and the like can be incorporated as required.

Invention modified NSAIDs contemplated for use in the practice of the present invention may also be administered in the form of suppositories for rectal administration of the drug. These compositions may be prepared by mixing the invention modified NSAIDs with a suitable non-irritating excipient, such as cocoa butter, synthetic glyceride esters of polyethylene glycols, which are solid at ordinary temperatures, but liquify and/or dissolve in the rectal cavity to release the drug.

Since individual subjects may present a wide variation in severity of symptoms and each drug has its unique therapeutic characteristics, the precise mode of administration and dosage employed for each subject is left to the discretion of the practitioner.

In general, the dosage of invention modified NSAIDs employed as described herein falls in the range of about 0.01 mmoles/kg body weight of the subject/hour up to about 0.5 mmoles/kg/hr. Typical daily doses, in general, lie within the range of from about 10 μg up to about 100 mg per kg body weight, and, preferably within the range of from 50 μg to 10 mg per kg body weight and can be administered up to four times daily. The daily IV dose lies within the range of from about 1 μg to about 100 mg per kg body weight, and, preferably, within the range of from 10 μg to 10 mg per kg body weight.

In accordance with yet another embodiment of the present invention, there are provided improved methods for the treatment of a subject suffering from a pathological condition by administration thereto of a NSAID, the improvement comprising covalently attaching said NSAID to a sulfur-containing functional group containing an optionally substituted hydrocarbyl moiety prior to administration thereof to said subject.

Thus, invention method for the treatment of a subject afflicted with a pathological condition comprises administering to a subject an effective amount of a modified pharmacologically active agent, wherein said pharmacologically active agent is a NSAID, and is effective for treatment of said condition, and wherein said pharmacologically active agent has been modified by the covalent attachment thereto a sulfur-containing functional group containing an optionally substituted hydrocarbyl moiety.

The invention will now be described in greater detail by reference to the following non-limiting examples.

The syntheses described in Examples 1–8 are outlined in Scheme 2.

Scheme 2

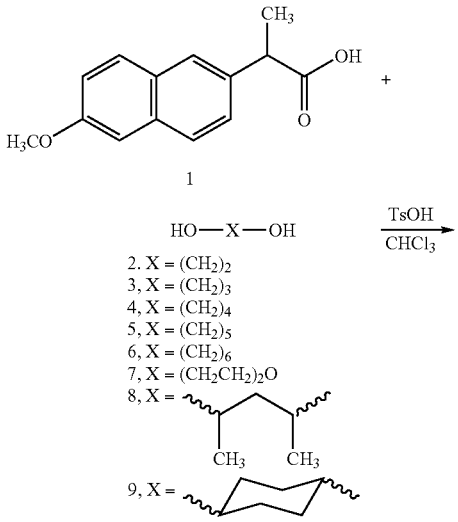

-continued

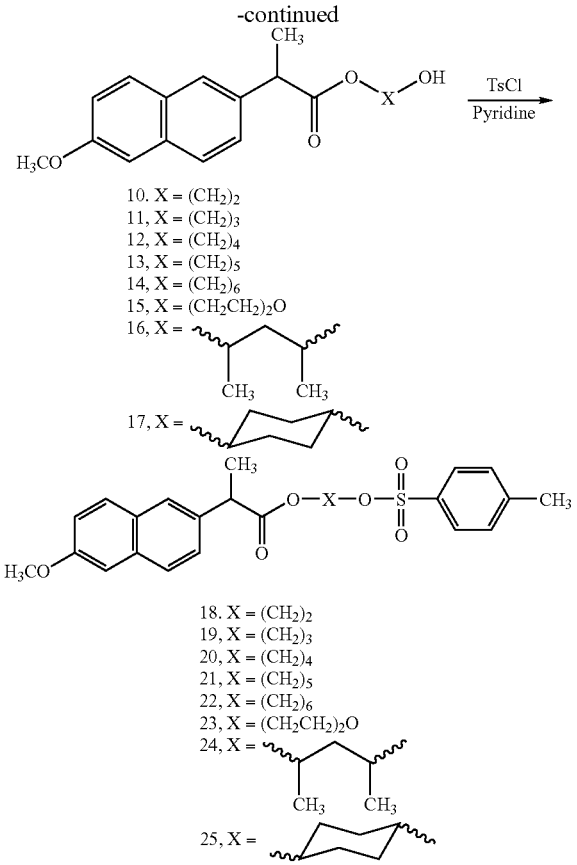

EXAMPLE 1

Compound 10 (Scheme 2). A mixture of Naproxen (1) (23 g, 0.1 mol), ethylene glycol (2) (27.9 ml, 0.5 mol) and toluenesulfonic acid (TsOH) (1.27 g, 6.7 mmol) in $CHCl_3$ was heated to reflux for 4 h. The reaction solution was washed with water, 10% $Na_2CO_3$ solution and water. The organic layer was dried ($Na_2SO_4$) and the solvent was evaporated. The residue was purified by crystallization from $CH_2Cl_2$ and hexanes to give 25.7 g (94%) of the compound 10 as a white crystal; $^1$H NMR ($CDCl_3$) δ 1.59 (d, 3H), 1.62 (br, 1H, ex $D_2O$), 3.74 (t, 2H), 3.90 (q, 1H), 3.91 (s, 3H), 4.21 (t, 2H), 7.11 (m, 2H), 7.39 (d, 1H), 7.69 (m, 3H); $^{13}$C NMR ($CDCl_3$) d 18.7, 45.6, 55.5, 61.4, 66.6, 105.8, 119.3, 126.1, 126.2, 127.5, 129.1, 129.5, 133.9, 135.7, 157.9, 175.2; MS (ESI) m/z 273 (M−1).

Compound 18 (Scheme 2). To a solution of compound 10 (24.5 g, 89 mmol) in 100 ml of pyridine was added tosyl chloride (TsCl) (34.1 g, 179 mmol). The resulting solution was stirred at 0° C. for 25 h. The reaction solution was then poured into 300 ml of water and then 200 ml of ether was added. The layers were separated and the organic phase was washed with water (300×5) and dried ($Na_2SO_4$). After the solvent was evaporated, the residue was purified by column chromatography on a silica gel column using dichloromethane as an eluent to give 35.1 g (92%) of the pale yellow oil; $^1$H NMR ($CDCl_3$) δ 1.55(d, 3H), 2.40 (s, 3H), 3.91 (q, 1H), 4.18 (m, 4H), 7.12 (m, 2H), 7.24 (m, 2H), 7.37 (d, 1H), 7.66 (d, 1H), 7.70 (m, 4H); MS (ESI) m/z 429 (M+1).

EXAMPLE 2

Compound 11 (Scheme 2). Compound 11 was prepared as described above for the preparation of compound 10, this time employing naproxen (1) and 1,3-propanediol (3). The resulting compound 11 was purified by crystallization from dichloromethane and hexanes with a 92% yield. $^1$H NMR ($CDCl_3$) δ 1.59 (d, 3H), 1.78 (m, 2H), 1.87 (br, 1H, $D_2O$ ex), 3.53 (t, 2H), 3.87 (q, 1H), 3.91 (s, 3H), 4.23 (t, 2H), 7.11 (d, 1H), 7.15 (m, 1H), 7.41 (q, 1H), 7.66 (d, 1H), 7.69 (s, 1H), 7.71 (s, 1H); $^{13}$C NMR ($CDCl_3$) δ 18.6, 31.8, 45.7, 55.5, 59.2, 61.9, 77.0, 77.2, 77.5, 105.8, 119.2, 126.1, 126.3, 127.4, 129.1, 129.4, 133.9, 135.7, 157.8, 175.3; and MS (ESI) m/z 289.4 (M+1).

Compound 19 (Scheme 2). Compound 19 was prepared as described above for the preparation of compound 18, this time employing compound 11 and TsCl. Compound 19 was purified by crystallization from ether and hexane with an yield of 95%; $^1$H NMR ($CDCl_3$) δ 1.54 (d, 3H), 1.91 (m, 2H), 2.42 (s, 3H), 3.79 (q, 1H), 3.92 (s, 3H), 3.99 (t, 2H), 4.10 (t, 2H), 7.11 d, 1H), 7.15 (q, 1H), 7.26 (d, 2H), 7.34 (d, 2H), 7.62(d, 1H), 7.70 (m, 4H); $^{13}$C NMR ($CDCl_3$) δ 18.5, 21.8, 28.4, 45.5, 55.5, 60.6, 66.9, 105.8, 119.2, 126.0, 126.3, 127.4, 128.0, 129.1, 129.5, 130.1, 133.1, 133.9, 135.6, 145.0, 157.9, 174.5; MS (ESI) m/z 421.1 (M−1).

EXAMPLE 3

Compound 12 (Scheme 2). Compound 12 was prepared as described above for the preparation of compound 10, this time employing naproxen (1) and 1,4-butanediol (4). Compound 12 was purified by crystallization from dichloromethane and hexanes with a 90% yield; $^1$H NMR ($CDCl_3$) δ 1.48 (m, 2H), 1.59 (d, 3H), 1.64 (m, 2H), 1.85 (s, 1H, $D_2O$, ex), 3.52 (t, 2H), 3.85 (q, 1H), 3.89 (s, 3H), 4.10 (t, 2H), 7.10–7.15 (m, 2H), 7.42 (, d, 1H), 7.66–7.7(m, 3H); MS (ESI) m/z 325.4 (M+Na).

Compound 20 (Scheme 2). Compound 20 was prepared as described above for the preparation of compound 18, this time employing compound 12 and TsCl. The compound 20 was purified by crystallization from ether and hexane with an yield of 93%; $^1$H NMR ($CDCl_3$) δ 1.55 (d, 3H), 1.53–1.62 (m, 4H), 2.43 (s, 3H), 3.82 (q, 1H), 3.92 (s, 3H), 3.94 (m, 2H), 4.02 (m, 2H), 7.11–7.15 (m, 2H), 7.30 (d, 2 h), 7.38 (d, 1H), 7.64 (d, 1H), 7.70 (d, 2H), 7.75 (d, 2H); MS (ESI) m/z 457.5 (M+1).

EXAMPLE 4

Compound 13 (Scheme 2). Compound 13 was prepared as described above for the preparation of compound 10, this time employing naproxen (1) and 1,5-pentanediol (5). After reaction, the reaction solution was washed with water and the reaction solvent was then evaporated under high vacuum to give a quantitative yield of the compound 13. The compound was used to make compound 21 without further purification. $^1$H NMR ($CDCl_3$) δ 1.28 (m, 2H), 1.46 (m, 2H), 1.55 (d, 3H), 1.59 (m, 2H), 3.51 (t, 2H), 3.85 (q, 1H), 3.91 (s, 3H), 4.09 (t, 2H), 7.11–7.15 (m, 2H), 7.40 (q, 1H), 7.66–7.70 (m, 3H); MS (ESI) m/z 317.5 (M+1).

Compound 21 (Scheme 2). Compound 21 was prepared as described above for the preparation of compound 18, this time employing compound 13 and TsCl. Compound 21 was purified by crystallization from ether and hexane with a 95% yield; $^1$H NMR ($CDCl_3$) δ 1.24 (m, 2H), 1.48–1.58 (m, 4H), 1.59 (d, 3H), 2.43 (s, 3H), 3.84 (q, 1H), 3.89 (t, 2H), 3.91 (s, 3H), 4.01 (t, 2H), 7.11–7.15 (m, 2H), 7.32 (q, 2H), 7.39 (q, 1H), 7.65 (d, 1H), 7.70 (m, 2H), 7.75 (d, 2H); MS (ESI) m/z 471.7 (M+1).

EXAMPLE 5

Compound 14 (Scheme 2). Compound 14 was prepared as described above for the preparation of compound 10, this time employing naproxen (1) and 1,6-hexanediol (6). After reaction, the reaction solution was washed with water and the reaction solvent was then evaporated to give compound 14 as a solid. The compound was used to make compound 22 without further purification; $^1$H NMR ($CDCl_3$) δ 1.24 (m, 4H), 1.43 (m 2H), 1.56 (d, 3H), 1.54 (m, 2H), 3.51 (t, 2H), 3.85 (q, 1H), 4.01 (m, 2H), 7.10–7.15 (m 2H), 7.40 (q, 1H), 7.66–7.70 (m, 3H); MS (ESI) m/z 331.7 (M+1).

Compound 22 (Scheme 22). Compound 22 was prepared as described above for the preparation of compound 18, this time employing compound 14 and TsCl. Compound 22 was purified by column chromatography on a silica gel column using dichloromethane as an eluent to give compound 22 as a pale yellow oil; The $^1$H NMR ($CDCl_3$) δ 1.12–1.22 (m, 4H), 1.46–1.52 (m, 4H), 1.57 (d, 3H), 2.43 (s, 3H), 3.84 (q, 1H), 3.92 (s, 3H), 3.93 (m, 2H), 4.03 (m, 2H), 7.11–7.77 (m, 10H); MS (ESI) m/z 485.6 (M+1).

EXAMPLE 6

Compound 15 (Scheme 2). Compound 15 was prepared as described above for the preparation of compound 10, this time employing naproxen (1) and di(ethylene glycol) (7). After reaction, the reaction solution was washed with water and the reaction solvent was then evaporated to give compound 15. The compound was used to make compound 23 without further purification; $^1$H NMR ($CDCl_3$) δ 1.58 (d, 3H), 1.93 (br, 1H, $D_2O$ ex), 3.43 (t, 2H), 3.59 (t, 2H), 3.62 (t, 2H), 3.89 (q, 1H), 3.90 (s, 3H), 4.25 (m, 2H), 7.11–7.15 (m, 2H), 7.40–7.42 (m, 1H), 7.70 (t, 3H); $^{13}$C NMR ($CDCl_3$) δ 18.7, 45.6, 55.5, 61.8, 64.0, 69.2, 72.4, 76.9, 77.2, 77.5, 105,7, 119.2, 126.2, 126.4, 127.3, 129.0, 133.9, 135.7, 157.9, 174.8; MS(ESI) m/z 319.3 (M+1).

Compound 23 (Scheme 2). Compound 23 was prepared as described above for the preparation of compound 18, this time employing compound 15 and TsCl. Compound 23 was purified by column chromatography on a silica gel column using dichloromethane as an eluent to give the compound as a pale yellow oil with a 93% yield. The $^1$H NMR ($CDCl_3$) δ 1.58 (d, 3H), 2.41 (s, 3H), 3.43 (m, 2H), 3.48(m, 2H), 3.84 (q, 1H), 3.86 (s, 3H), 3.94 (t, 2H), 4.10 (m, 2H), 7.10–7.13 (m, 2H), 7.29 (d, 2H), 7.39 (d, 1H), 7.65–7.75 (m, 5H); $^{13}$C NMR ($CDCl_3$) δ 18.6, 21.8, 45.5, 55.5, 63.9, 68.7, 69.27, 69.27, 105.8, 119.2, 126.2, 126.4, 127.4, 128.1, 129.0, 129.4, 129.9, 133.9, 145.0, 157.9, 174.7; MS (ESI) m/z 473.4 (M+1).

EXAMPLE 7

Compound 16 (Scheme 2). Compound 16 was prepared as described above for the preparation of compound 10, this time employing naproxen (1) and 1,3-pentanediol (8). After reaction, the reaction solution was washed with water and the reaction solvent was then evaporated to give compound 15 with a 32% yield. The compound was used to make compound 24 without further purification; $^1$H NMR, $^{13}$C NMR and MS are consistent with the structure of compound 16.

Compound 24 (Scheme 2). Compound 24 was prepared as described above for the preparation of compound 18, this time employing compound 16 and TsCl. The compound 24 was purified by column chromatography on a silica gel column using dichloromethane as an eluent to give the compound as a pale yellow oil with a 82% yield. The $^1$H NMR, $^{13}$C NMR and MS are consistent with the structure of compound 24.

EXAMPLE 8

Compound 17 (Scheme 2). Compound 17 was prepared as described above for the preparation of compound 10, this time employing naproxen (1) and 1,4-cyclohexanediol (8). After reaction, the reaction solution was washed with water and the reaction solvent was then evaporated to give compound 17. Compound 17 was used to make compound 25 without further purification; $^1$H NMR ($CDCl_3$) δ 1.30–1.45 (m, 6H), 1.56 (d, 3H), 1.80–1.98 (m, 4H), 3.66 (m, 1H), 3.82 (q, 1H), 3.91 (s, 3H), 4.75 (m, 1H), 7.11 m, 2H), 7.39 (d, 1H), 7.65–7.70 (m, 3H); $^{13}$C NMR ($CDCl_3$) 18.7, 28.2, 28.5, 32.1, 32.2, 45.9, 55.5, 68.9, 72.0, 76.9, 77.2, 77.5, 105.8, 119.1, 126.0, 126.4, 127.2, 129.1, 129.5, 133.8, 136.1, 157.8, 174.4; MS (ESI) m/z 351.4 (M+Na).

Compound 25 (Scheme 2). Compound 25 was prepared as described above for the preparation of compound 18, this time employing compound 17 and TsCl. Compound 25 was purified by column chromatography on a silica gel column using dichloromethane as an eluent to give the compound as a pale yellow oil with a 93% yield; $^1$H NMR ($CDCl_3$) δ 1.50–1.84 (m, 11H), 2.43 (s, 3H), 3.80 (q, 1H), 3.92 (s, 3H), 4.51 (m, (1H), 4.78 (m, 1H), 7.10–7.15 (m, 2H), 7.26–7.39 (m, 3H), 7.61–7.75 (m, 5H), MS (ESI) m/z 483.5 (M+H).

The syntheses described in Examples 9–14 are outlined in Scheme 3.

Scheme 3

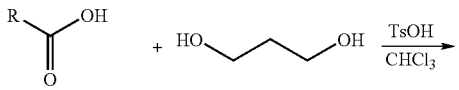

26, R = Ketoprofen
27, R = Flurbiprofen
28, R = Ibuprofen
29, R = Diclofenac
30, R = Carprofen
31, R = Indomethacin

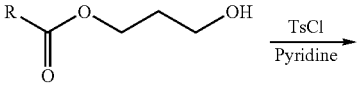

32, R = Ketoprofen
33, R = Flurbiprofen
34, R = Ibuprofen
35, R = Diclofenac
36, R = Carprofen
37, R = Indomethacin -continued

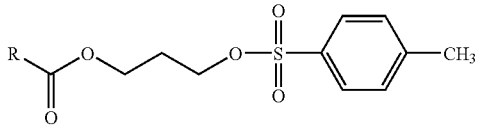

38, R = Ketoprofen
39, R = Flurbiprofen
40, R = Ibuprofen
41, R = Diclofenac
42, R = Carprofen
43, R = Indomethacin

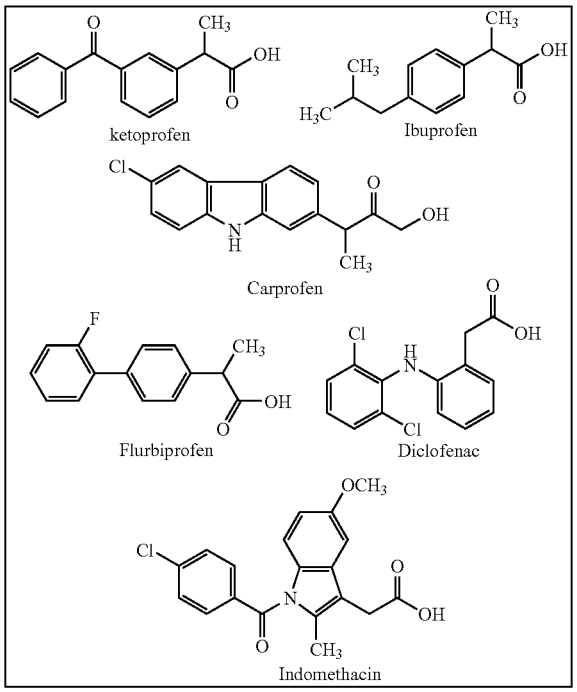

EXAMPLE 9

Compound 32 (Scheme 23). Compound 32 was prepared as described above for the preparation of compound 10, this time employing ketoprofen (26) and 1,3-propanediol (3). Compound 32 was purified by column chromatography on a silica gel column using 200:1 $CH_2Cl_2$/MeOH as an eluent to give compound 32 with a 50% yield. $^1$H NMR ($CDCl_3$) δ 1.55 (d, 3H), 1.82 (m 3H, 1H, $D_2O$ ex), 3.58 (m, 2H), 3.82 (m, 1H), 4.25 (m 2H), 7.44–7.82 (m, 9H); MS (ESI) m/z 313.5 (M+H).

Compound 38 (Scheme 3). Compound 38 was prepared as described above for the preparation of compound 18, this time employing compound 32 and TsCl. Compound 38 was purified by column chromatography on a silica gel column using $CH_2Cl_2$ as an eluent to give the compound 38 as a colorless oil with a 81% yield; $^1$H NMR ($CDCl_3$) δ1.49 (d, 3H), 1.94 (m, 2H), 2.43 (s, 3H), 3.72 (q, 1H), 4.01 (t, 2H), 4.12 (m, 2H), 7.31–7.78 (m, 13H); MS (ESI) m/z 467.3 (M+H).

EXAMPLE 10

Compound 33 (Scheme 3). Compound 33 was prepared as described above for the preparation of compound 10, this time employing flurbiprofen (27) and 1,3-propanediol (3). After reaction, the reaction solution was washed in water and the reaction solvent was then evaporated to give the compound 33 with a quantitative yield. The compound 33 was used to make compound 39 without further purification; $^1$H NMR ($CDCl_3$) δ 1.54 (d, 3H), 1.79 (t, 1H, $D_2O$ ex), 1.85 (m, 2H), 3.63 (m, 2H), 3.76 (q, 1H), 4.27 (t, 2H), 7.11–7.16 (m, 2H), 7.35–7.46 (m, 4H), 7.54 (d, 2H); MS (ESI) m/z 325.4 (M+Na).

Compound 39 (Scheme 3). Compound 39 was prepared as described above for the preparation of compound 18, this time employing compound 33 and TsCl. Compound 39 was purified by crystallization from ether/hexane system with a 79% yield; $^1$H NMR ($CDCl_3$) δ 1.59 (d, 3H), 1.96 (m, 2H), 2.42 (s, 3H), 3.68 (q, 1H), 4.03 (t, 2H), 4.15 (t, 2H), 7.05–7.11 (m, 2H), 7.25–7.54 (m, 8H), 7.76 (d, 2H); $^{13}$C NMR ($CDCl_3$) δ 18.4, 21.8, 28.4, 45.0, 50.8, 66.9, 115.2, 115.5, 123.68, 123.7, 127.9, 128.0, 129.2, 130.1, 131.0, 133.1, 135.6, 141.75, 141.8, 145.1, 158.9, 160.9, 173.9; MS (ESI) m/z 479.4 (M+Na).

EXAMPLE 11

Compound 34 (Scheme 3). Compound 34 was prepared as described above for the preparation of compound 10, this time employing ibuprofen (28) and 1,3-propanediol (3). After reaction, the reaction solution was washed in water and the reaction solvent was then evaporated to give compound 34 with a quantitative yield. The compound 34 was used to make compound 40 without further purification; $^1$H NMR ($CDCl_3$) δ 0.89 (d, 6H), 1.49 (d, 3H), 1.79 (t, 2H), 1.78–1.85 (m, 1H), 1.95 (t, 1H, $D_2O$ ex), 2.45 (d, 2H), 3.53 (m, 2H), 3.71 (q, 1H), 4.22 (m, 2H), 7.09 (d, 2H), 7.26 (d, 2H).

Compound 40 (Scheme 3). Compound 40 was prepared as described above for the preparation of compound 18, this time employing compound 34 and TsCl. Compound 40 was purified by crystallization from ether/hexane system to give a white solid with a 96% yield; $^1$H NMR ($CDCl_3$) δ 0.89 (d, 6H), 1.44 (d, 3H), 1.81–1.92 (m, 3H), 2.44 (s, 3H), 3.61 (q, 1H), 3.99 (t, 2H), 4.09 (t, 2H), 7.08 (d, 2H), 7.14 (d, 2H), 7.34 (d, 2H), 7.78 (d, 2H); $^{13}$C NMR ($CDCl_3$) d 18.46, 21.80, 22.54, 28.39, 30.32, 45.16, 60.39, 66.92, 127.23, 128.04, 129.50, 130.03, 133.12, 137.68, 140.76, 145.00, 174.54; MS (ESI) m/z 441.5 (M+Na).

EXAMPLE 12

Compound 35 (Scheme 3). Compound 35 was prepared as described above for the preparation of compound 10, this time employing diclofenac (29) and 1,3-propanediol (3). After reaction, compound 35 was purified by column chromatography on a silica gel column using 200:1 $CH_2Cl_2$/MeOH as an eluent to give the compound 35 as a white solid with a 56% yield. $^1$H NMR ($CDCl_3$) δ 1.89 (m, 3H, 1H $D_2O$ ex), 3.66 (t, 2H), 3.83 (s, 3H), 4.31 (t, 2H), 6.55 (d, 1H), 6.87 (br, 1H), 6.94–7.00 (m, 2H), 7.11–7.14 (m, 1H), 7.22–7.26 (m, 1H), 7.34 (d, 2H); MS (ESI) m/z 376.3 (M+Na).

Compound 41 (Scheme 3). Compound 41 was prepared as described above for the preparation of compound 18, this time employing compound 35 and TsCl. Compound 41 was purified by column chromatography on a silica gel column using $CH_2Cl_2$ as an eluent to give the compound 41 as a pale yellow oil and the yield was 89%; $^1$H NMR ($CDCl_3$) δ 2.02 (m, 2H), 2.43 (s, 3H), 3.73 (s, 2H), 4.09 (t, 2H), 4.17 (t, 2H), 6.53 (d, 1H), 6.99 (s, 1H), 6.93–7.00 (m, 2H), 7.12 (t, 1H), 7.18 (d, 1H), 7.23 (d, 1H), 7.31–7.35 (m, 3H), 7.78 (d, 2H); MS (ESI) m/z 508.3 (M).

EXAMPLE 13

Compound 36 (Scheme 3). Compound 36 was prepared as described above for the preparation of compound 10, this time employing carprofen (30) and 1,3-propanediol (3). After reaction, compound 36 was purified by column chromatography on a silica gel column using 200:1 $CH_2Cl_2$/MeOH as an eluent to give the compound 36 as a colorless oil with a 54% yield. $^1$H NMR ($CDCl_3$) δ 1.59 (d, 3H), 1.74 (br, 1H, $D_2O$ ex), 1.80 (m, 2H), 3.53–3.56 (m, 2H), 3.88 (q, 1H), 4.22–4.28 (m, 2H), 7.17 (d, 1H), 7.29–7.35 (m, 3H), 7.94–7.98 (m, 2H), 8.14 (br, 1H); $^{13}$C NMR ($CDCl_3$) δ 18.99, 31.84, 46.17, 59.42, 62.10, 109.70, 111.79, 119.79, 120.21, 129.87, 121.92, 124.49, 125.22, 126.09, 138.24, 139.37, 140.55, 175.39; MS (ESI) m/z 332.2 (M+H).

Compound 42 (Scheme 3). Compound 42 was prepared as described above for the preparation of compound 18, this time employing compound 36 and TsCl. Compound 42 was purified by column chromatography on a silica gel column using $CH_2Cl_2$ as an eluent to give the compound 42 as a sticky oil and the yield was 90%; The $^1$H NMR ($CDCl_3$) δ 1.55 (d, 3H), 1.91 (m, 2H), 2.39 (s, 3H), 3.83 (q, 1H), 3.97 (t, 2H), 4.09–4.18 (m, 2H), 7.10 (d, 1H), 7.21 (d, 2H), 7.32 (s, 2H), 7.38 (s, 1H), 7.65 (d, 2H), 7.91 (d, 1H), 7.98 (s, 1H), 8.54 (s, 1H); $^{13}$C NMR ($CDCl_3$) δ 18.83, 21.77, 28.32, 46.08, 60.59, 57.04, 109.97, 111.97, 119.58, 120.06, 120.69, 121.77, 124.38, 125.00, 125.99, 127.95, 129.22, 130.06, 132.90, 138.38, 139.19, 140.69, 145.15, 174.59; MS (ESI) m/z 486.3 (M+H).

EXAMPLE 14

Compound 37 (Scheme 3). Compound 37 was prepared as described above for the preparation of compound 10, this time employing indomethacin (31) and 1,3-propanediol (3). After reaction, compound 37 was purified by column chromatography on a silica gel column using 200:1; 100:1 $CH_2Cl_2$/MeOH as an eluents to give the compound 37 as a pale yellow oil with a 49% yield. $^1$H NMR, $^{13}$CNMR and MS are consistent with the structure of compound 37.

Compound 43 (Scheme 3). Compound 43 was prepared as described above for the preparation of compound 18, this time employing compound 37 and TsCl. The compound 43 was purified by column chromatography on a silica gel column using hexane/ethyl acetate (3:1) as an eluent to give the compound 43 as a pale yellow oil and the yield was 71%; $^1$H NMR ($CDCl_3$) δ 1.97 (m, 2H), 2.36 (s, 3H), 2.44 (s, 3H), 3.63 (s, 2H), 3.83 (s, 3H), 4.05 (t, 2H), 4.15 (t, 2H), 6.66–6.68 (m, 1H), 6.87 (d, 1H), 6.93 (d, 1H), 7.33 (d, 2H), 7.47 (d, 2H), 7.67 (d, 2H), 7.75 (d, 2H); MS (ESI) m/z 592.0 (M+Na).

The syntheses described in Examples 15 and 16 are outlined in Scheme 4.

Scheme 4

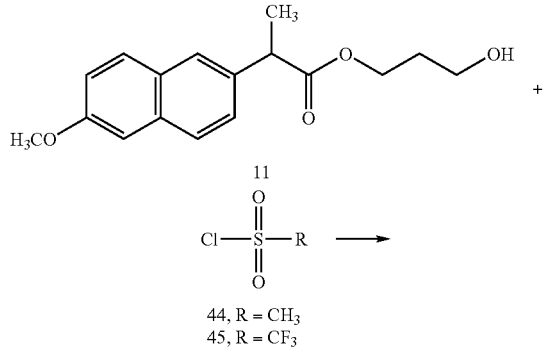

-continued

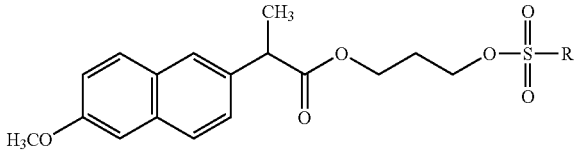

46, R = $CH_3$
47, R = $CF_3$

EXAMPLE 15

Compound 46 (Scheme 4). Compound 46 was prepared as described above for the preparation of compound 18, this time employing compound 11 and 44. The compound 46 was purified by crystallization from ether/hexane system to give the compound 46 as a white solid. The yield was 95%; $^1$H NMR ($CDCl_3$) δ 1.58 (d, 3H), 2.00 (m, 2H), 2.73 (s, 3H), 3.87 (q, 1H), 3.90 (s, 3H), 4.10 (t, 2H), 4.18 (t, 2H), 7.10–7.15 (m, 2H), 7.39 (d, 1H), 7.66–7.71 (m, 3H); $^{13}$C NMR ($CDCl_3$) δ 18.46, 28.55, 37.03, 45.56, 55.47, 55.50, 60.38, 66.36, 105.75, 119.32, 126.09, 126.27, 127.44, 129.06, 129.41, 133.89, 135.68, 157.91, 174.59; MS (ESI) m/z 388.5 (M+Na).

EXAMPLE 16

Compound 47 (Scheme 4). Compound 47 is prepared as described above for the preparation of compound 18, this time employing compound 11 and compound 45. The compound is purified by crystallization and the yield was 70–90%. The $^1$H NMR, $^{13}$C NMR and MS are consistent with the structure of compound 47.

The syntheses described in Examples 17 and 18 are outlined in Scheme 5.

Scheme 5

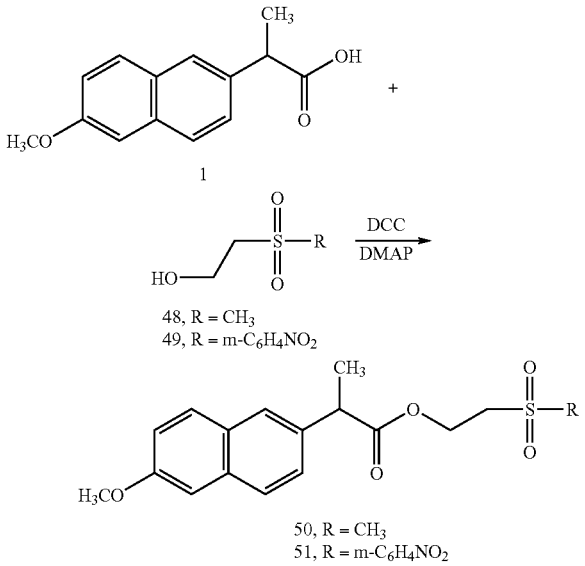

48, R = $CH_3$
49, R = m-$C_6H_4NO_2$

50, R = $CH_3$
51, R = m-$C_6H_4NO_2$

EXAMPLE 17

Compound 50 (Scheme 5). To a solution of naproxen (1) (1.15 g, 5 mmol), compound 48 (0.62 g, 5 mmol) and dimethylamino pyridine (DMAP) (0.12 g, 1 mmol) was added dicyclohexyldicarbodiimide (DCC) (1.03 g, 5 mmol) at 0° C. The resulting solution was stirred at 0° C. for 1.5 h. After reaction, the solid was filtered off and the solvent was evaporated. The residue was washed with ether to give 1.4 g (83%) of compound 50 as a white solid; $^1$HNMR ($CDCl_3$) δ 1.59 (d, 3H), 2.38 (s, 3H), 3.17 (m, 2H), 3.87 (q, 1H), 3.92 (s, 3H), 4.43 (m, 1H), 4.59 (m, 1H), 7.10 (d, 1H), 7.15 (m, 1H), 7.33 (m, 1H), 7.67 (d, 1H), 7.70 (m, 2H); MS (ES) m/e 358.2 (M+Na).

EXAMPLE 18

Compound 51 (Scheme 5). Compound 51 was prepared as described above for the preparation of compound 50, this time employing compound 1 (1.15 g, 5 mmol) and 49 (1.16 g, 5 mmol). The compound was purified by column chromatography on a silica gel column using 1:1 hexanes/ethyl acetate as eluent to give 0.91 g of compound 51 as a pale yellow oil; $^1$HNMR ($CDCl_3$) δ 1.45 (d, 3H), 3.48 (m, 2H), 3.59 (q, 1H), 3.92 (s, 3H), 4.47 (m, 2H), 7.10 (d, 1H), 7.18 (m, 2H), 7.45 (s, 1H), 7.49 (t, 1H), 7.65 (t, 2H), 8.06 (q, 1H), 8.28 (q, 1H), 8.68 (s, 1H); $^{13}$C NMR ($CDCl_3$) 18.8, 45.2, 55.4, 55.5, 57.9, 105,8, 123.6, 125.9, 127.5, 128.4, 129.0, 129.3, 130.8, 133.7, 133.9, 134.9, 141.5, 148.4, 158.0, 174.0.

The syntheses described in Examples 19–21 are outlined in Scheme 6.

Scheme 6

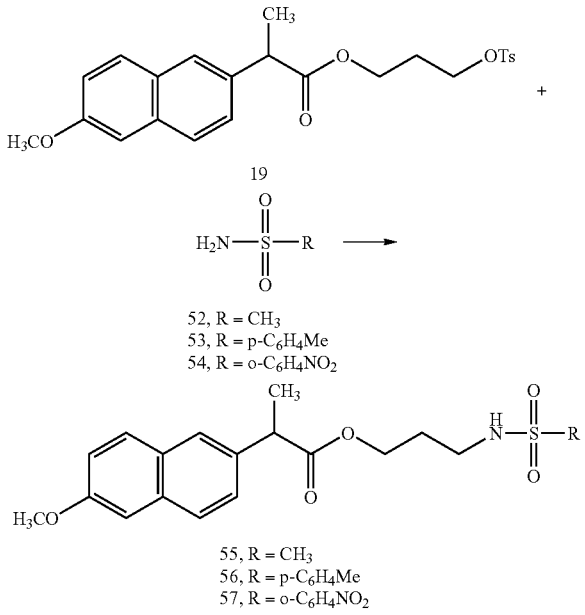

52, R = $CH_3$
53, R = p-$C_6H_4Me$
54, R = o-$C_6H_4NO_2$

55, R = $CH_3$
56, R = p-$C_6H_4Me$
57, R = o-$C_6H_4NO_2$

EXAMPLE 19

Compound 55 (Scheme 6). A mixture of compound 19 (2.2 g, 5 mmol), compound 52 (0.57 g, 6 mmol) and $K_2CO_3$ (3.45 g, 25 mmol) in 50 ml of dimethyl formamide (DMF) was stirred for a week. The reaction solution was poured into 100 ml of water and extracted with $CH_2Cl_2$. The organic phase was washed with water (50×5) and dried ($Na_2SO_4$). The solvent was evaporated and the residue was purified by column chromatography on a silica gel column using 3:1 hexane/ethyacetate as an eluent to give 0.3 g (16%) of compound 55 as a pale yellow oil; $^1$HNMR ($CDCl_3$) δ 1.60 (d, 3H), 2.38 (s, 3H), 3.17 (m, 2H), 3.87 (q, 1H), 3.92 (s, 3H), 4.45 (m, 1H), 4.59 (m, 1H), 7.10 (s, 1H), 7.14–7.16 (q, 1H), 7.32–7.35 (q, 1H), 7.62 (s, 1H), 7.67–7.71 (m, 2H); MS (ESI) m/z 358.2 (M+Na).

EXAMPLE 20

Compound 56 (Scheme 6). Compound 56 was prepared as described above for the preparation of compound 55, this time employing compound 19 and compound 53. The compound was purified by column chromatography on a silica gel column using $CH_2Cl_2$ as an eluent to give compound 56 as a pale yellow oil (33%). $^1$HNMR ($CDCl_3$) δ 1.54 (d, 3H), 1.72 (m, 2H), 2.83 (m, 2H), 3.80 (q, 1H), 3.92 (s, 3H), 4.10 (t, 2H) 7.07–8,10 (m, 10H); MS (ESI) m/z 442.3 (M+H).

EXAMPLE 21

Compound 57 (Scheme 6). Compound 57 was prepared as described above for the preparation of compound 55, this time employing compound 19 and compound 54. The compound was purified by column chromatography on a silica gel column using $CH_2Cl_2$ as an eluent to give compound 57 as a pale yellow oil (11%). The $^1$HNMR ($CDCl_3$) δ 1.55 (d, 3H), 1.80 (m, 2H), 3.03 (m 2H), 3.86 (m, 1H), 4.13 (m, 2H), 7.07–7.93 (m, 10H); MS (ESI) m/z 473.4 (M+H).

Scheme 7

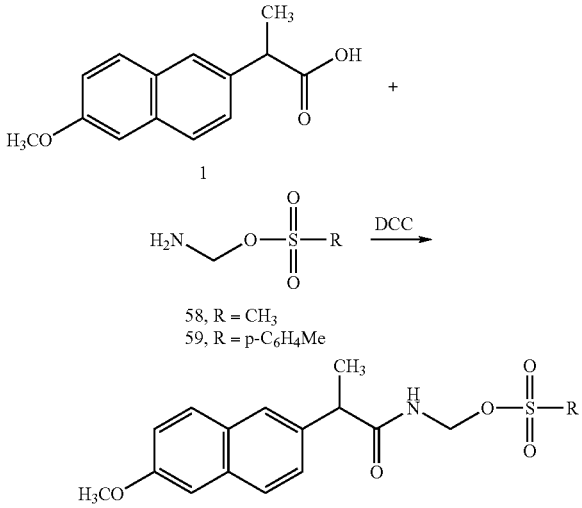

EXAMPLE 22

Compound 60 (Scheme 7). Compound 60 is prepared as described above for the preparation of compound 50, this time employing naproxen 1 and compound 58. After reaction the compound is purified by column chromatography on a silica gel column to give the compound 60 in a yield from 75–95%.

EXAMPLE 23

Compound 61 (Scheme 7). Compound 61 is prepared as described above for the preparation of compound 50, this time employing naproxen (1) and compound 59. After reaction, the compound is purified by column chromatography on a silica gel column to give compound 61 in a yield from 75–95%.

The syntheses described in Examples 24 and 25 are outlined in Scheme 8.

Scheme 8

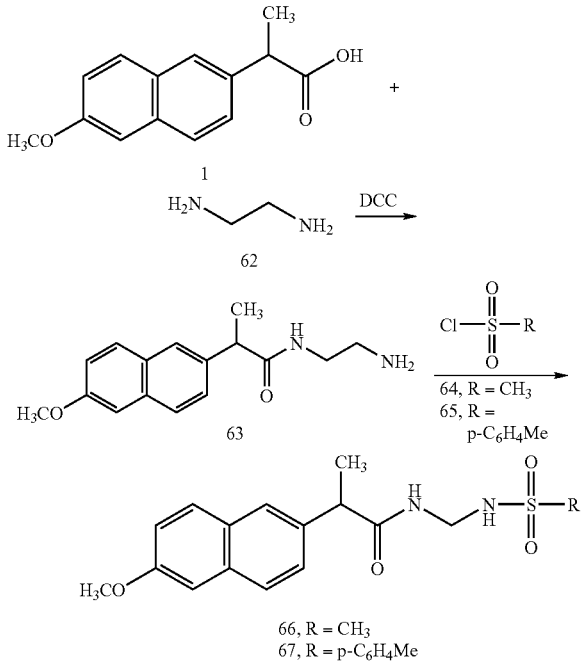

EXAMPLE 24

Compound 63 (Scheme 8). Compound 63 is prepared as described above for the preparation of compound 50, this time employing naproxen (1) and compound 62. After reaction, the compound is purified by column chromatography on a silica gel column to give compound 63 in a yield of 75–95%.

Compound 66 (Scheme 8). Compound 66 is prepared as described above for the preparation of compound 18, this time employing compound 63 and compound 64.

EXAMPLE 25

Compound 67 (Scheme 8). Compound 67 is prepared as described above for the preparation of compound 18, this time employing compound 63 and compound 65.

The syntheses described in Examples 26 and 27 are outlined in Scheme 9.

Scheme 9

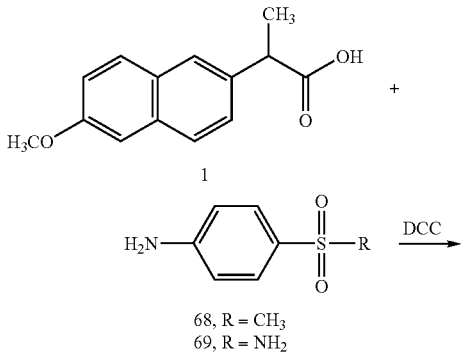

-continued

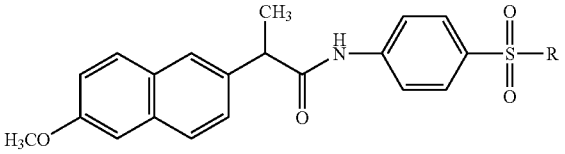

70, R = $CH_3$
71, R = $NH_2$

EXAMPLE 26

Compound 70 (Scheme 9). Compound 70 is prepared as described above for the preparation of compound 60, this time employing compound 1 and compound 68.

EXAMPLE 27

Compound 71 (Scheme 9). Compound 71 is prepared as described above for the preparation of compound 60, this time employing compound 1 and compound 69.

The syntheses described in Example 28 is outlined in Scheme 10.

Scheme 10

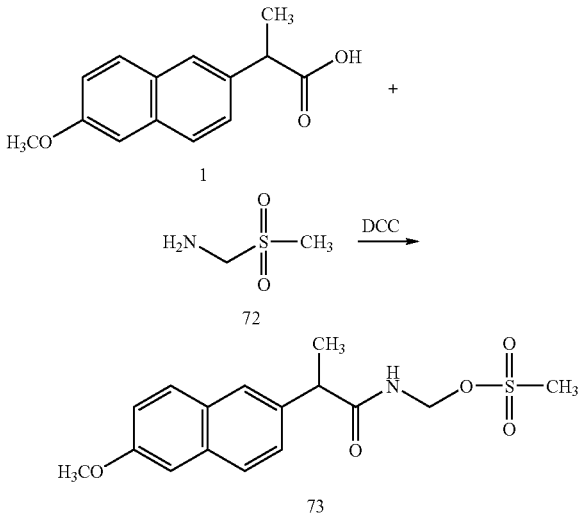

EXAMPLE 28

Compound 73 (Scheme 10). Compound 73 is prepared as described above for the preparation of compound 60, this time employing compound 1 and compound 72.

The synthesis described in Example 29 is outlined in Scheme 11.

Scheme 11

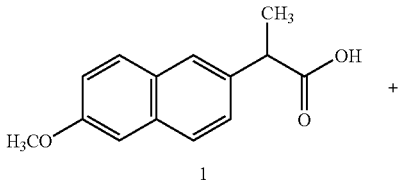

-continued

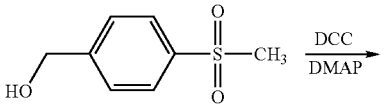

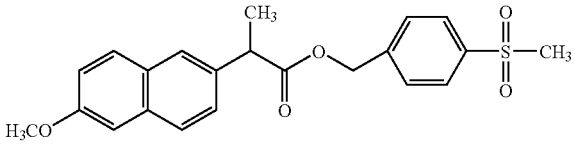

EXAMPLE 29

Compound 75 (Scheme 11). Compound 75 is prepared as described above for the preparation of compound 60, this time employing compound 1 and compound 74.

EXAMPLE 30

Reduced Numbers of Intestinal Ulcers in Rat Acute and Subacute Enteropathy Models by the Invention Modified NSAID (compound 19), a Prodrug of Naproxen NSAIDs are important drugs used to treat acute and chronic inflammation as well as pain and fever. The major limitation to NSAID use is the occurrence of gastrointestinal ulcers and erosions. These side effects are produced by a combination of local and systemic effects. Attempts have been made to circumvent the local side effects of NSAIDs by making them as prodrugs, which will bypass the stomach, but so far this has not been clearly successful. It is demonstrated here that the invention modified NSAIDs substantially reduce GI toxicity, while exhibiting dose equivalent efficacy in anti-inflammation activity in both acute and chronic inflammation animal models.

Sprague-Dawley rats (male, 150–200 g), were orally dosed once daily for either 3 days (acute model) or 14 days (subacute model). Twenty-four hours after the last dose, the rats were injected i.v. with Evans Blue (5 ml/kg, 10 mg/ml) to stain the ulcers. Ten to twenty minutes later the animals were sacrificed by $CO_2$ inhalation and the intestines removed, opened lengthwise and the contents removed. The long dimensions of all ulcers were measured using a ruler and summed to give a total ulcer source.

Figure 2:
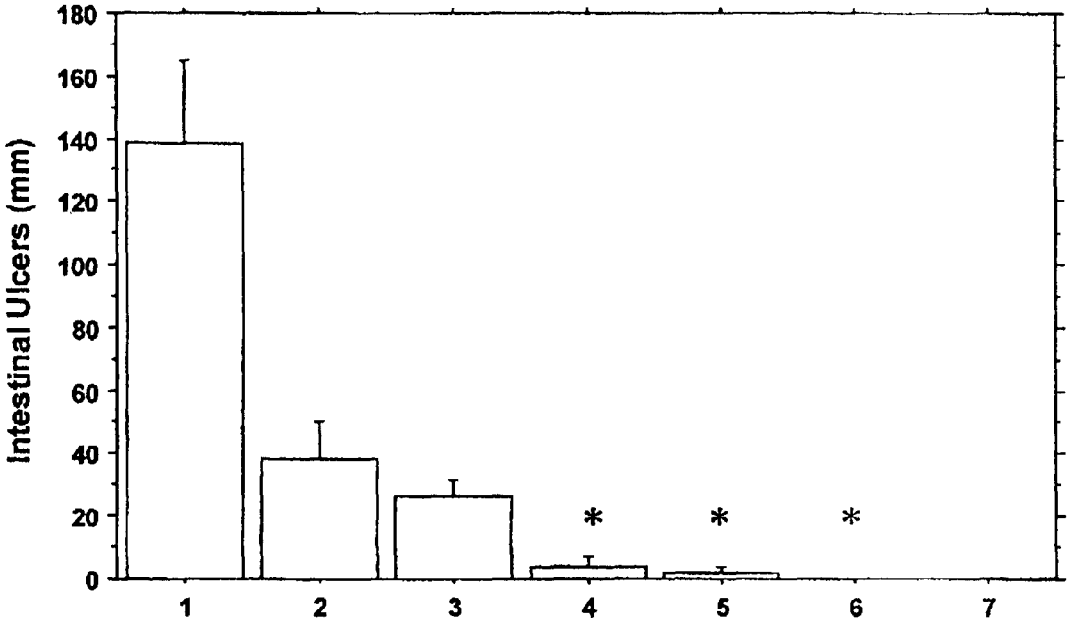
FIG. 2 illustrates the total length of intestinal ulcers measured after 14 daily doses of NSAID in unfasted male Sprague-Dawley rats (150–200 g) treated with vehicle (bar 7), three doses of naproxen (bar 1: 50 mg/kg, bar 2: 45 mg/kg, bar 3: 40 mg/kg), or three equimolar doses of invention composition (compound 19) (bars 4–6). * $P<0.05$ by unpaired t-test vs. corresponding dose of naproxen.

In the acute model (FIG. 1), ulceration after dosing with an invention modified NSAID (compound 19) was 15% of that seen with an equimolar dose of naproxen. PEG had no ulcerogenic effect. In the subacute model (FIG. 2), ulceration was less than 5% of that seen with a corresponding dose of naproxen at all three doses used. Again, PEG had no effect. These results suggest that invention modified NSAIDs are much less ulcerogenic than naproxen.

EXAMPLE 31
M

Reduction of Chronic Hindlimb Inflammation in the Rat Adjuvant Arthritis Model by the Invention Modified NSAID (compound 19), a Prodrug of Naproxen NSAIDs are useful in the treatment of both chronic and acute inflammatory conditions. Efficacy in chronic inflammation can be estimated using the rat adjuvant arthritis model. In this model Lewis male rats (175–250 g) are injected intradermally in the footpad with M. tuberculosis powder suspended in mineral oil at 5 mg/ml. Progressive swelling of the uninjected paw and ankle joint between days 5 and 15 is measured by plethysmometry.

Figure 3:
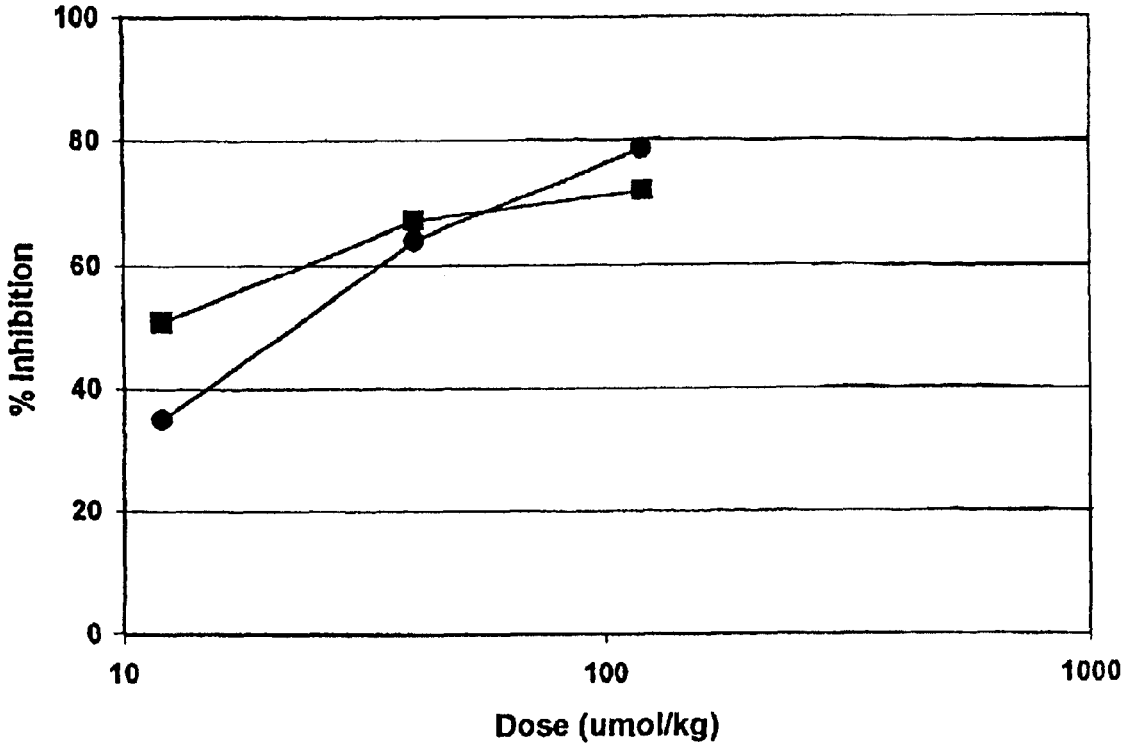
FIG. 3 illustrates the inhibition of paw volume increases in the uninjected feet of Lewis male rats in which arthritis was induced by intradermal injection of adjuvant into the footpad. Rats were injected on day 0 and treated once daily from days 8 to 15 with vehicle, naproxen (10 mg/kg), or invention composition (compound 19) at equivalent dose. Paw volumes were measured with a Plethysmometer on days 5 and 15. Closed circles=naproxen; squares=invention composition.

Rats were dosed daily by oral gavage with 5 ml/kg of naproxen at 3 to 30 mg/kg in phosphate buffered saline (PBS) and with equimolar doses of an invention modified NSAID at 1 ml/kg in PEG 300. The results (FIG. 3) show that the invention modified NSAID resulted in antiinflammatory effects comparable to those of naproxen in this model.

EXAMPLE 32

Reduction of Acute Hindlimb Inflammation in the Rat Carrageenan-induced Hindlimb Edema Model by the Invention Modified NSAID (compound 19), a Prodrug of Naproxen Efficacy of NSAIDs in acute inflammation can be estimated by using intraplanar injection of carrageenan in the rat. Sprague-Dawley rats (200–250 g male) are injected intradermally in the footpad with 50 μl of a 1% carrageenan solution in PBS. Swelling of the injected paw is measured 3 & 4 hours later, using a plethysmometer.

Pretreatment with oral naproxen one hour before the carrageenan injection at 10 mg/kg resulted in an approximately 50% reduction in swelling at both time points (Table 1). An equimolar dose of an invention modified NSAID reduced inflammation to the same degree at both time points. These results suggest that invention modified NSAIDs are comparable in effect to naproxen at 10 mg/kg.

TABLE 1

Effects of naproxen and the invention modified NSAID (compound 19) on paw volume increase in carrageenan-induced inflammation in rats.

| Treatment | 4 Hours | 5 Hours |
|---|---|---|
| Vehicle | 0.73 ± 0.10 | 0.85 ± 0.10 |
| Naproxen (1 mg/kg) | 0.63 ± 0.07 | 0.75 ± 0.08 |
| Naproxen (10 mg/kg) | 0.32 ± 0.05* | 0.39 ± 0.07* |
| Compound 19 (1.75 mg/kg) | 0.78 ± 0.04 | 0.93 ± 0.04 |
| Compound 19 (17.5 mg/kg) | 0.34 ± 0.06* | 0.40 ± 0.06* |

*P < 0.05 vs Vehicle by unpaired t-test.

Invention modified NSAIDs are seen to have antiinflammatory activity similar to naproxen in the chronic adjuvant arthritis and acute carrageenan hindlimb edema rat models. The tendency to cause intestinal ulcers is reduced substantially invention modified NSAID. Thus, invention modified NSAIDs provide an effective prodrug form of naproxen with reduced intestinal side effects.

EXAMPLE 33

Plasma Pharmacokinetics of Naproxen and the Invention Modified NSAID After Oral Administration in Rats The invention compound (compound 19) is a naproxen prodrug, which is a conjugate of naproxen and tosylate. Oral administration of the invention compound resulted in the release of free naproxen. The pharmacokinetics of naproxen release from the invention modified NSAID and its parent drug, naproxen, was evaluated in rats after oral administration.

The carotid artery of Sprague-Dawley rat (250–350 g, male) was catheterized at least one day before drug administration and flushed with 30% polyvinyl pyrrolidone (PVP) (400 U/mL of heparin) to maintain patency. At predetermined time points (see Table 2), blood samples (250 μL) were collected by unhooking the flushing syringe and letting the flood flow out of the catheter and into the centrifuge tubes. After centrifugation (13,000 rpm, 10 min, 4° C.), the plasma samples were collected and analyzed in the same day.

TABLE 2

Rat group assignment and doses

| Test Article | Group # | Rat # | Dose* (mg/kg) | Sample Time |
|---|---|---|---|---|
| Naproxen | 1 | 1, 2, 3, & 4 | Oral (2 mg/kg) | 5 min, 0.5, 1, 4, 7, 10, 13, 16, 19, 22, & 24 hrs |
| Invention Compound 19 | 2 | 5, 6, 7, & 8 | Oral (2 mg/kg) | 15 min, 0.5, 1, 3, 5, 6, 7, 8, 22, 23, & 24 hrs |

*Indicates amount of naproxen in dose.

Aliquot of plasma sample (100 μL) was mixed with 200 μL of acetonitrile. After vortexing and centrifugation (13,000 rpm, 10 min, 4° C.), 200 μL of supernatant was removed and added to 300 μL of a 58:42 mixture of 50 mM phosphate buffer (pH 5.0) and acetonitrile. Following vortexing and centrifugation, 25 μL of supernatant was removed and analyzed by HPLC with a UV detection system.

The average plasma concentration at each time point was calculated and utilized in a pharmacokinetic analysis. Noncompartmental pharmacokinetic analysis was carried out using WinNolin (Pharsight, Mountainview, Calif.) to calculate the maximum concentration ($C_{max}$), time to maximum concentration ($T_{max}$), area under the curve from zero to the last time point ($AUC_{last}$), the area under the curve from zero to infinite time ($AUC_{inf}$), and the terminal phase half life (Beta-$t_{1/2}$).

The $AUC_{all}$, $AUC_{INF}$, and $t_{1/2}$ of naproxen from naproxen and a modified form of naproxen according to the invention were found to be similar (Table 3). On the other hand, for the invention modified form of neproxen, the $C_{max}$ was lower and the $T_{max}$ longer, compared to naproxen (see Table 3).

TABLE 3

| Non-Compartmental Pharmacokinetic Analysis of naproxen and the invention modified form of naproxen according to the (compound 19) after oral administration in rats | | | | | | | |
|---|---|---|---|---|---|---|---|
| Drug | Dose* (mg/kg) | $C_{max}$ (μg/mL) | $T_{max}$ (hrs) | $AUC_{all}$ (μg * ht/mL) | $AUF_{INF}$ | $t_{1/2}$ (hrs) | N |
| Naproxen | 2 | 7.77 ± 4.13 | 0.5 ± 0.5 | 50 ± 6 | 55 ± 7 | 6.2 ± 0.4 | 4 |
| Invention modified naproxen | 2 | 3.87 ± 1.05 | 6.8 ± 1.5 | 49 ± 10 | 56 ± 14 | 6.8 ± 2.7 | 4 |

*Indicates amount of naproxen in dose.

Following oral naproxen administration, the naproxen plasma levels were at the highest at the first time-point (5 minutes) then declined in a bi-exponential manner. In contrast, after oral administration of a modified form of naproxen according to the invention, the maximum naproxen levels were observed at a much later time ($T_{max}$ of 6.8±1.5 hrs). The similar $AUC_{all}$, $AUC_{INF}$, and $T_{1/2}$ values but lower $C_{max}$ and longer $T_{max}$ values supports the conclusions drawn from the results obtained from pharmacological studies, i.e. that a modified form of naproxen according to the invention conjugate has equivalent pharmacological efficacy and greatly improved gastrointestinal safety profile compared to naproxen.

While the invention has been described in detail with reference to certain preferred embodiments thereof, it will be understood that modifications and variations are within the spirit and scope of that which is described and claimed.

That which is claimed is:

[1. A compound having the structure:

X—L—Z wherein:

X=a non-steroidal anti-inflammatory drug (NSAID),

L=a covalent bond, a linker, or a spacer,

Z=a sulfur-containing functional group containing a substituted or unsubstituted hydrocarbyl moiety, wherein the sulfur-containing functional group is sulfoxide, sulfonate, reverse sulfonate, sulfonamide, reverse sulfonamide, sulfone, sulfinate, or reverse sulfinate.]

[2. A compound according to claim 1 wherein said NSAID is acetaminophen, aspirin, ibuprofen, choline magnesium salicylate, choline salicylate, diclofenac, diflunisal, etodolac, fenprofen calcium, flurobiprofen, indomethacin, ketoprofen, carprofen, indoprofen, ketorolac tromethamine, magnesium salicylate, meclofenamate sodium, mefenamic acid, oxaprozin, piroxicam, sodium salicylate, sulindac, tolmetin, meloxicam, nabumetone, naproxen, lornoxicam, nimesulide, indoprofen, remifenzone, salsalate, tiaprofenic acid, or flosulide.]

[3. A compound according to claim 2 wherein said NSAID is diclofenac, naproxen, aspirin, ibuprofen, flurbiprofen, indomethacin, ketoprofen, or carprofen.]

[4. A compound according to claim 1 wherein the sulfur-containing functional group is sulfoxide.]

[5. A compound according to claim 1 wherein the sulfur-containing functional group is sulfonate or reverse sulfonate.]

[6. A compound according to claim 5 wherein the sulfur-containing functional group is a substituted or unsubstituted aromatic solfonate.]

[7. A compound according to claim 6 wherein said aromatic sulfonate is tosylate or brosylate.]

[8. A compound according to claim 5 wherein the sulfur-containing functional group is a substituted or unsubstituted C1 to C10 alkyl sulfonate.]

[9. A compound according to claim 8 wherein the alkyl sulfonate is mesylate or triflate.]

[10. A compound according to claim 1 wherein the sulfur containing functional group is a sulfone.]

[11. A compound according to claim 10 wherein the sulfur-containing functional group is a substituted or unsubstituted C1 to C10 alkyl sulfone.]

[12. A compound according to claim 11 wherein said sulfone is methyl sulfone, ethyl sulfone.]

[13. A compound according to claim 10 wherein the sulfur-containing functional group is a substituted or unsubstituted aromatic sulfone.]

[14. A compound according to claim 13 wherein the sulfur-containing functional group is a p-substituted aromatic sulfone.]

[15. A compound according to claim 1 wherein the sulfur-containing functional group is a sulfonamide or reverse sulfonamide.]

[16. A compound according to claim 15 wherein the sulfur-containing functional group is a substituted or unsubstituted C1 to C10 alkyl sulfonamide.]

[17. A compound according to claim 16 wherein the sulfur-containing functional group is methyl sulfonamide.]

[18. A compound according to claim 15 wherein the sulfur-containing functional group is a substituted or unsubstituted aromatic sulfonamide.]

[19. A compound according to claim 18 wherein the sulfur-containing functional group is toluene sulfonamide.]

[20. A compound according to claim 1 wherein the sulfur-containing functional group is a sulfinate or reverse sulfinate.]

[21. A compound according to claim 1 wherein L has the structure:

—W—R— wherein:

R is present or absent, and when present is alkylene, substituted alkylene, cycloalkylene, substituted cycloalkylene, heterocyclic, substituted heterocyclic, oxyalkylene, substituted oxyalkylene, alkenylene, substituted alkenylene, arylene, substituted arylene, alkarylene, substituted alkarylene, aralkylene or substituted aralkylene, and W is ester, reverse ester, thioester, reverse thioester, amide, reverse amide, phosphate, phosphonate, imine or enamine.]

[22. A formulation comprising a compound according to claim 1 in a pharmaceutically acceptable carrier therefor.]

[23. A formulation according to claim 22 wherein said pharmaceutically acceptable carrier is a solid, solution, emulsion, dispersion, micelle or liposome.]

[24. A formulation according to claim 22 wherein said pharmaceutically acceptable carrier further comprises an enteric coating.]

[25. In a method for the administration of a non-steroidal anti-inflammatory drug (NSAID) to a subject for the treatment of a pathological condition, the improvement comprising directly or indirectly covalently attaching said NSAID to a sulfur-containing functional group containing a substituted or unsubstituted hydrocarbyl moiety prior to administration thereof to said subject.]

[26. The method of claim 25 wherein said pathological condition is septic shock, hemorrhagic shock, anaphylactic shock, toxic shock syndrome, ischemia, cerebral ischemia, administration of cytokines, overexpression of cytokines, ulcers, inflammatory bowel disease, diabetes, arthritis, asthma, Alzheimer's disease, Parkinson's disease, multiple sclerosis, cirrhosis, allograft rejection, encephalomyelitis, meningitis, pancreatis, peritonitis, vasculitis, lymphocytic choriomeningitis, glomerulonephritis, uveitis, ileitis, inflammation, burn, infection, hemodialysis, chronic fatigue syndrome, stroke, cancers, cardiopulmonary bypass, ischemic/reperfusion injury, gastritis, adult respiratory distress syndrome, cachexia, myocarditis, autoimmune disorders, eczema, psoriasis, heart failure, heart disease, atherosclerosis, dermatitis, urticaria, systemic lupus erythematosus, AIDS, AIDS dementia, chronic neurodegenerative disease, chronic pain, priapism, cystic fibrosis, amyotrophic lateral sclerosis, schizophrenia, depression, premenstrual syndrome, anxiety, addiction, migraine, Huntington's disease, epilepsy, neurodegenerative disorders, gastrointestinal motility disorders, obesity, hyperphagia, solid tumors, malaria, hematologic cancers, myelofibrosis, lung injury, graft-versus-host disease, head injury, CNS trauma, hepatitis, renal failure, liver disease, drug-induced lung injury, myasthenia gravis (MG), ophthalmic diseases, post-angioplasty, restenosis, angina, or coronary artery disease.]

[27. In the treatment of a subject suffering from a pathological condition by administration thereto of a non-steroidal anti-inflammatory drug (NSAID), the improvement comprising covalently attaching said NSAID to a sulfur-containing functional group containing a substituted or unsubstituted hydrocarbyl moiety prior to administration thereof to said subject.]

[28. A method for the treatment of a subject afflicted with a pathological condition, said method comprising administering to said subject an effective amount of a non-steroidal anti-inflammatory drug (NSAID), wherein said NSAID is effective for treatment of said condition, and wherein said NSAID has been modified by the direct or indirect covalent attachment thereto of a sulfur-containing functional group containing a substituted or unsubstituted hydrocarbyl moiety.]

[29. A method for the preparation of a protected form of a non-steroidal anti-inflammatory drug (NSAID), said method comprising directly or indirectly covalently attaching a sulfur-containing functional group containing a substituted or unsubstituted hydrocarbyl moiety to said NSAID.]

[30. A method according to claim 29 wherein said NSAID is acetaminophen, aspirin, ibuprofen, choline magnesium salicylate, choline, salicylate, diclofenac, diflunisal, etodolac, fenprofen calcium, flurbiprofen, indomethacin, ketoprofen, carprofen, indoprofen, ketorolac tromethamine, magnesium salicylate, meclofenamate sodium, mefenamic acid, oxaprozin, piroxicam, sodium salicylate, sulindac, tolmetin, meloxicam, nabumetone, naproxen, lornoxicam, nimesulide, indoprofen, remifenzone, salsalate, tiaprofenic acid, or flosulide.]

[31. A method for reducing the side effects induced by administration of a non-steroidal anti-inflammatory drug (NSAID) to a subject, said method comprising directly or indirectly covalently attaching a sulfur-containing functional group containing a substituted or unsubstituted hydrocarbyl moiety to said NSAID prior to administration to said subject.]

[32. A method for enhancing the effectiveness of a non-steroidal anti-inflammatory drug (NSAID), said method comprising directly or indirectly covalently attaching a sulfur-containing functional group containing a substituted or unsubstituted hydrocarbyl moiety to said NSAID.]

[33. A method for the prevention or treatment of an inflammatory or infectious disease in a subject in need thereof, said method comprising administering to said subject an amount of the compound of claim 1 effective to alleviate said condition.]

*34. A compound having the structure:*

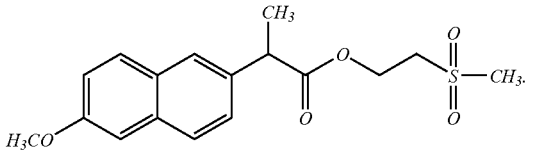

*35. A pharmaceutical composition comprising a prodrug of naproxen of the formula:*

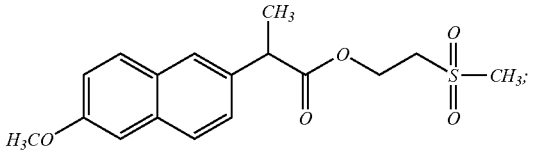

*and a pharmaceutically acceptable carrier.*

*36. The pharmaceutical composition of claim 35, wherein the pharmaceutical composition is in the form of a tablet.*

*37. A pharmaceutical composition comprising a pharmaceutically effective amount of a compound of the formula:*

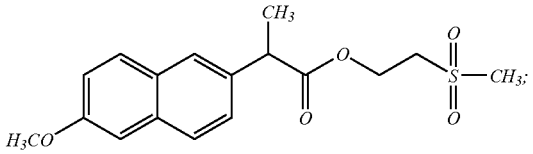

*and a pharmaceutically acceptable carrier.*

*38. A method for delivering naproxen to a subject comprising:*

*administering to the subject an effective amount of a prodrug, the prodrug having a formula of:*

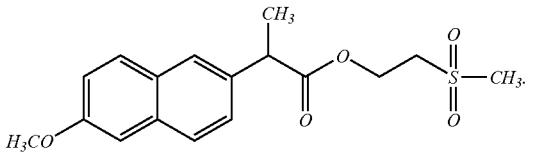

*39. The method of claim 38, wherein the effective amount of the prodrug is formulated into a pharmaceutical composition.*

*40. The method of claim 39, wherein the pharmaceutical composition is a tablet.*

*41. The method of claim 38, wherein an effective amount of naproxen is delivered to the subject.*

* * * * *